(12) United States Patent
Nakamura et al.

(10) Patent No.: US 8,182,997 B2
(45) Date of Patent: May 22, 2012

(54) PROSTATE CANCER RELATED GENE STYK1

(75) Inventors: Yusuke Nakamura, Bunkyo-ku (JP);
Hidewaki Nakagawa, Bunkyo-ku (JP);
Shuichi Nakatsuru, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 103 days.

(21) Appl. No.: 12/376,714

(22) PCT Filed: Aug. 8, 2007

(86) PCT No.: PCT/JP2007/065895
§ 371 (c)(1),
(2), (4) Date: Jun. 14, 2010

(87) PCT Pub. No.: WO2008/018625
PCT Pub. Date: Feb. 14, 2008

(65) Prior Publication Data
US 2011/0135654 A1    Jun. 9, 2011

Related U.S. Application Data

(60) Provisional application No. 60/836,799, filed on Aug. 9, 2006.

(51) Int. Cl.
*G01N 33/53* (2006.01)
*C12Q 1/68* (2006.01)
(52) U.S. Cl. .................................. 435/7.1; 435/6.1
(58) Field of Classification Search .................. None
See application file for complete search history.

(56) References Cited

U.S. PATENT DOCUMENTS

| | | |
|---|---|---|
| 2003/0027227 A1 | 2/2003 | Lin |
| 2005/0259483 A1 | 11/2005 | Nakamura et al. |

FOREIGN PATENT DOCUMENTS

| | | |
|---|---|---|
| WO | WO 2005/113816 A2 | 12/2005 |
| WO | WO 2006/036941 A2 | 4/2006 |

OTHER PUBLICATIONS

Tockman et al (Cancer Res., 1992, 52:2711s-2718s).*
Liu et al (Cancer Research, 2004, 64: 3491-3499).*
Anastasia, K., et al., EMBL database Accession No. ADQ60942, 1 pg (Sep. 9, 2004).
Blum, H., et al., EMBL database Accession No. AL353940, 2 pgs. (Apr. 27, 2000).
Chung, et al., "Identification of a kinase over-expressed in hormone refractory prostate cancer cells and its possibility of therapeutic target for prostate cancer," *Proceedings of the Sixty-Fifth Annual Meeting of the Japanese Cancer Association*, p. 54(#0-110) (Aug. 28, 2006).
Floryk, D., et al., "Differentiation of Androgen-Independent Prostate Cancer PC-3 Cells Is Associated with Increased Nuclear Factor-κB Activity," *Cancer Res.*, vol. 65(24), pp. 11588-11596 (Dec. 15, 2005).
Ye, X., et al., "Isolation and characterization of a human putative receptor protein kinase cDNA STYK1," *Molecular Biology Reports*, vol. 30(2), pp. 91-96 (Jun. 2003).

* cited by examiner

*Primary Examiner* — Sean Aeder
(74) *Attorney, Agent, or Firm* — Kilpatrick Townsend & Stockton LLP

(57) ABSTRACT

The present invention provides methods for detecting and diagnosing cancer, which method involves the determination of the expression level of the STYK1 gene. The gene was discovered to discriminate cancer cells from normal cells. Furthermore, the present invention provides methods of screening for therapeutic agents useful in the treatment of cancer, methods for treating cancer, and methods for vaccinating a subject against cancer. Moreover, the present invention provides siRNAs targeting the STYK1 gene, which are suggested to be useful in the treatment of cancer.

4 Claims, 3 Drawing Sheets

Fig 2
A
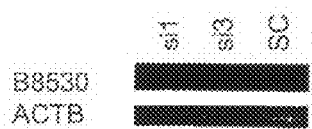
D
B
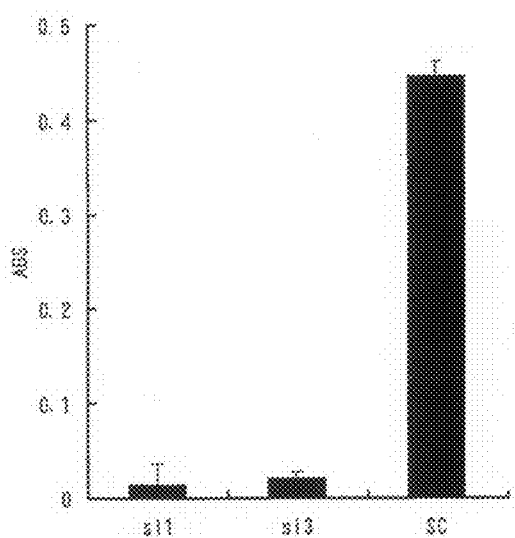
E
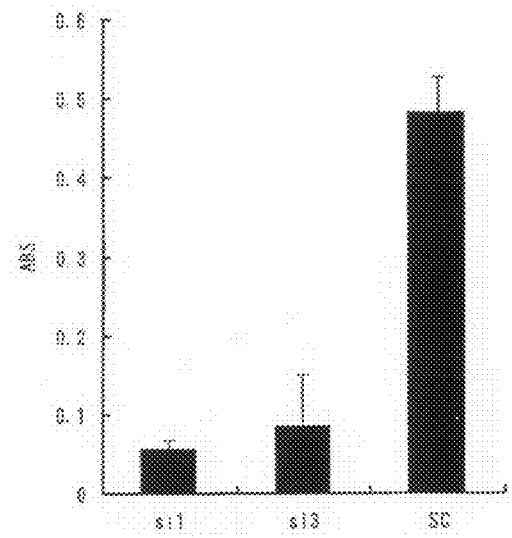
C
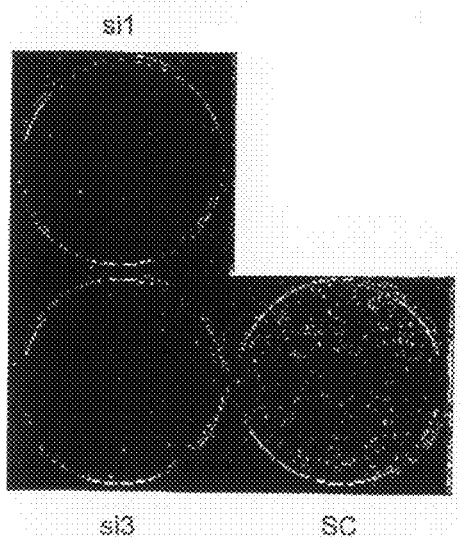
F
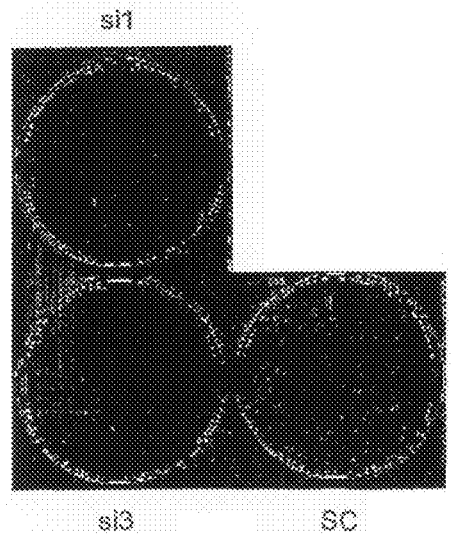

Fig. 3
A
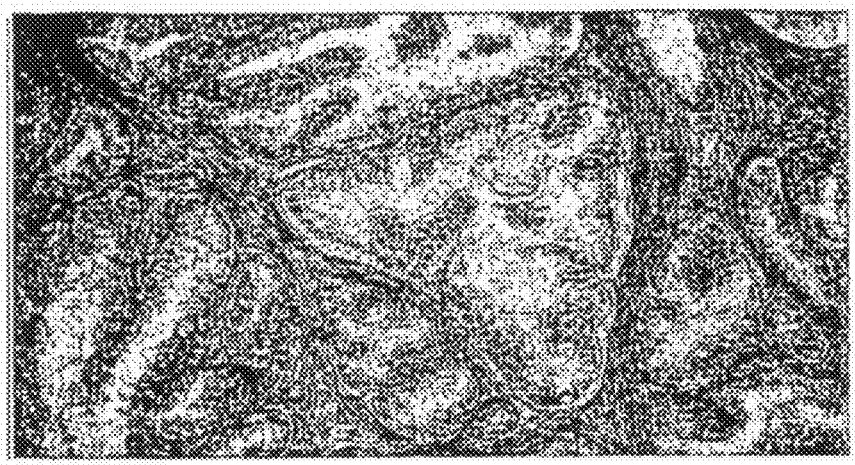
B
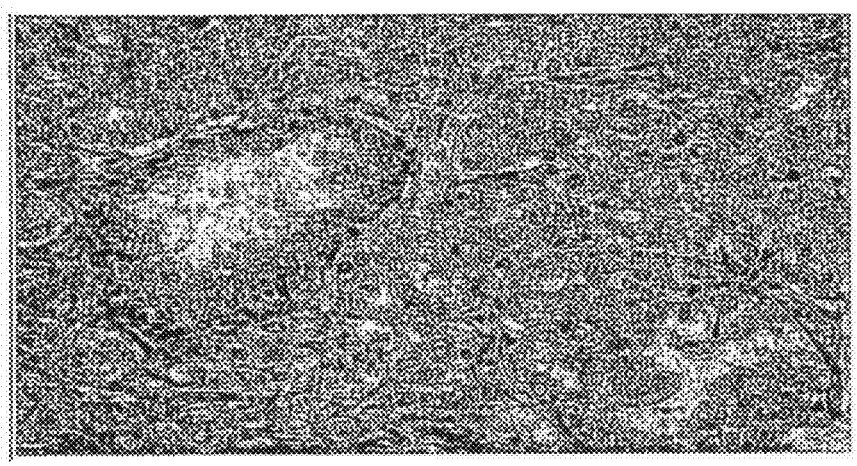
C
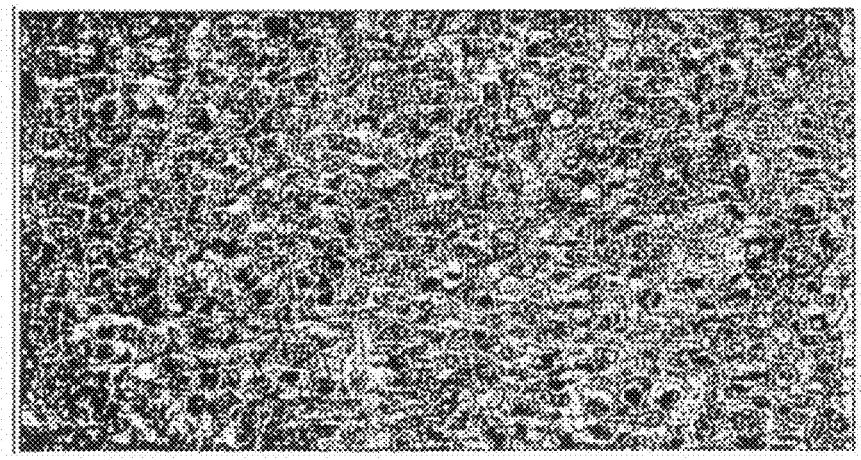

PROSTATE CANCER RELATED GENE STYK1

The present application is a U.S. National Stage Application of PCT/JP2007/065895, filed Aug. 8, 2007, which claims the benefit of U.S. Provisional Application No. 60/836,799 filed Aug. 9, 2006, the contents of which are herein incorporated by reference.

TECHNICAL FIELD

The present invention relates to methods for detecting and diagnosing prostate cancer as well as methods for treating and preventing prostate cancer.

BACKGROUND ART

Prostate cancer (PC) is the most common malignancy in males and the second leading cause of cancer-related deaths in the United States and Europe (Gronberg H. Lancet 2003 Mar. 8, 361(9360): 859-64). Detection of PC at an early stage by serum test for prostate specific antigen (PSA), and subsequent surgery and radiation therapy can cure the localized disease, but nearly 30% of treated PC patients suffer relapse (Han M, Partin A W, et al. J Urol 2001, 166: 416-9; Roberts S G, et al. Mayo Clin Proc 2001, 76: 576-81; Roberts W W, et al. Urology 2001, 57: 1033-7).

Despite high response rates and clinical benefits, androgen ablation therapy does not cure advanced or relapsed prostate cancer, because hormone refractory prostate cancer (HRPC) cells inevitably emerge and lead to cancer death. There are no effective treatments available for such HRPCs at present, and identification of novel molecular targets and therapeutic approach targeting them are urgently required. These HRPC cells not only grow hormone-independently, but also behave more aggressively as cancer cells and lead patients to death, which implicate that a number of other growth-promoting or malignant signaling pathways, bypassing the androgen receptor (AR) pathway, are activated in HRPC as well as AR signaling (Grossmann M E, et al. JNCI 2001, 93: 1687-97; Craft N, et al. Nature Med 1999, 5: 280-5; Bernard D, et al. JCI 2003, 112: 1724-31).

DISCLOSURE OF THE INVENTION

The present invention is based on the discovery of a specific expression pattern of the STYK1 gene in cancerous cells.

Through the present invention, the STYK1 gene was revealed to be frequently up-regulated in human tumors, in particular, prostate cancer including hormone refractory prostate cancer (HRPC). Moreover, since the suppression of the STYK1 gene by small interfering RNA (siRNA) resulted in growth inhibition and/or cell death of HRPC cells, this gene was suggested to serve as a novel therapeutic target for human prostate cancers.

The STYK1 gene identified herein as well as its transcription and translation products find diagnostic utility as a marker for prostate cancer and as an oncogene target, the expression and/or activity of which may be altered to treat or alleviate a symptom of cancer. Similarly, by detecting the changes in the expression of the STYK1 gene due to a compound, various compounds can be identified as agents for treating or preventing cancer.

Accordingly, the present invention provides a method for diagnosing or determining a predisposition to prostate cancer in a subject by determining the expression level of the STYK1 gene in a subject-derived biological sample, such as tissue sample. Increased expression level of the gene as compared to a normal control level indicates that the subject suffers from or is at risk of developing prostate cancer. The normal control level can be determined using a normal cell obtained from a non-cancerous tissue. In the present invention, preferred prostate cancer to be diagnosed is hormone refractory prostate cancer (HRPC).

In the context of the present invention, the phrase "control level" refers to the expression level of the STYK1 gene detected in a control sample and includes both normal control level and cancer control level. A control level can be a single expression pattern derived from a single reference population or the average calculated from a plurality of expression patterns. Alternatively, the control level can be a database of expression patterns from previously tested cells. A "normal control level" refers to a level of the STYK1 gene expression detected in a normal healthy individual or in a population of individuals known not to be suffering from cancer. A normal individual is one with no clinical symptom of prostate cancer. A "normal control level" may also be the expression level of the STYK1 gene detected in a normal healthy tissue or cell of an individual or population known not to be suffering from prostate cancer. On the other hand, a "cancer control level" refers to an expression level of the STYK1 gene detected in the cancerous tissue or cell of an individual or population suffering from prostate cancer.

An increase in the expression level of the STYK1 gene detected in a sample as compared to a normal control level indicates that the subject (from which the sample has been obtained) suffers from or is at risk of developing prostate cancer.

Alternatively, expression level of the STYK1 gene in a sample can be compared to cancer control level of the STYK1 gene. A similarity between the expression level of a sample and the cancer control level indicates that the subject (from which the sample has been obtained) suffers from or is at risk of developing cancer.

Herein, gene expression levels are deemed to be "altered" when the gene expression increases by, for example, 10%, 25%, or 50% from, or at least 0.1 fold, at least 0.2 fold, at least 0.5 fold, at least 2 fold, at least 5 fold, or at least 10 fold or more compared to a control level. The expression level of the STYK1 gene can be determined by detecting, e.g., hybridization intensity of nucleic acid probes to gene transcripts in a sample.

In the context of the present invention, subject-derived tissue samples may be any tissues obtained from test subjects, e.g, patients known to have or suspected of having cancer. For example, tissues may comprise epithelial cells. More particularly, tissues may be cancerous epithelial cells.

The present invention further provides methods for identifying compounds that inhibit the expression or activity of the STYK1 protein, by contacting a test cell expressing the STYK1 protein with test compounds and determining the expression level of the STYK1 gene or the activity of the gene product, the STYK1 protein. The test cell may be an epithelial cell, such as cancerous epithelial cell. A decrease in the expression level of the gene or the activity of its gene product as compared to a control level in the absence of the test compound indicates that the test compound may be used to reduce symptoms of prostate cancer.

The present invention also provides a kit that comprises at least one detection reagent which binds to the transcription or translation product of the STYK1 gene.

Therapeutic methods of the present invention include methods for treating or preventing prostate cancer in a subject comprising the step of administering an antisense composition to the subject. In the context of the present invention, the antisense composition reduces the expression of the STYK1 gene. For example, the antisense compositions may contain a nucleotide which is complementary to the STYK1 gene sequence. Alternatively, the present methods may include the step of administering siRNA composition to the subject. In the context of the present invention, the siRNA composition reduces the expression of the STYK1 gene. In yet another method, the treatment or prevention of prostate cancer in a subject may be carried out by administering a ribozyme composition to the subject. In the context of the present invention, the nucleic acid-specific ribozyme composition reduce the expression of the STYK1 gene.

Actually, the present inventors confirmed inhibitory effects of siRNAs for the STYK1 gene. For example, the inhibition of cell proliferation of cancer cells by the siRNAs are demonstrated in the Examples section, which supports the fact that the STYK1 gene serves as a preferable therapeutic target for prostate cancer. Thus, the present invention also provides double-stranded molecules which serve as siRNAs against the STYK1 gene as well as vectors expressing the double-stranded molecules.

The present invention also includes vaccines and vaccination methods. For example, a method for treating or preventing prostate cancer in a subject may involve administering to the subject a vaccine containing a polypeptide encoded by the STYK1 gene or an immunologically active fragment of the polypeptide. In the context of the present invention, immunologically active fragments are polypeptides that are shorter in length than the full-length naturally-occurring protein yet which induce an immune response analogous to that induced by the full-length protein. For example, an immunologically active fragment should be at least 8 amino acid residues in length and capable of stimulating an immune cell such as a T cell or a B cell. Immune cell stimulation can be measured by detecting cell proliferation, elaboration of cytokines (e.g., IL-2), or production of an antibody.

One advantage of the methods described herein is that the disease is identified prior to detection of overt clinical symptoms of prostate cancer. Other features and advantages of the invention will be apparent from the following detailed description, and from the claims.

BRIEF DESCRIPTION OF THE DRAWINGS

FIG. 2 shows the knockdown of STYK1 by siRNA which lead to attenuated PC cell viability. Two STYK1 siRNA expression vectors (si1 and si3) and a scramble siRNA expression vector (negative control) were transfected into 22Rv1 (A, B, and C) and LNCaP cells (D, E, and F) which overexpress STYK1. Knockdown effect on STYK1 transcript was validated by RT-PCR (A and D), with ACTB expression as a quantitative control. STYK1-si1 and -si3 revealed strong knockdown effect, while scramble siRNA did not show any effect on the level of endogenous STYK1 transcript. Transfection with STYK1-si1 and -si3 resulted in drastic reduction of the numbers of viable cells measured by MTT assay (B and E) and the number of colony formation (C and F), compared with the cells transfected with siRNA expression vector (scramble siRNA) which did not show any knockdown effect on STYK1. The results of the MTT assay are shown in panels B and E, and ABS on the Y-axis is abbreviation of 'absorbance' indicating that the numbers of viable cells were detected as the absorbance at 490 nm, and at 630 nm as reference, with a microplate reader.

FIG. 3 shows the immunohistochemical analysis of clinical prostate cancer (PC) tissues. (A) The immunohistochemical analysis of normal prostate epithelium in PC tissues was shown. The positivity of STYK1 was week. (B) The immunohistochemical analysis of hormone-sensitive or naïve PCs was shown. 14/16 (88%) showed the week positivity of STYK1. (C) The immunohistochemical analysis of STYK1 positive tissue was shown. All of six HRPCs and 2/16 (15%) of hormone-sensitive or naïve PC showed strong positivity of STYK1.

DETAILED DESCRIPTION OF THE INVENTION

Figure 1:
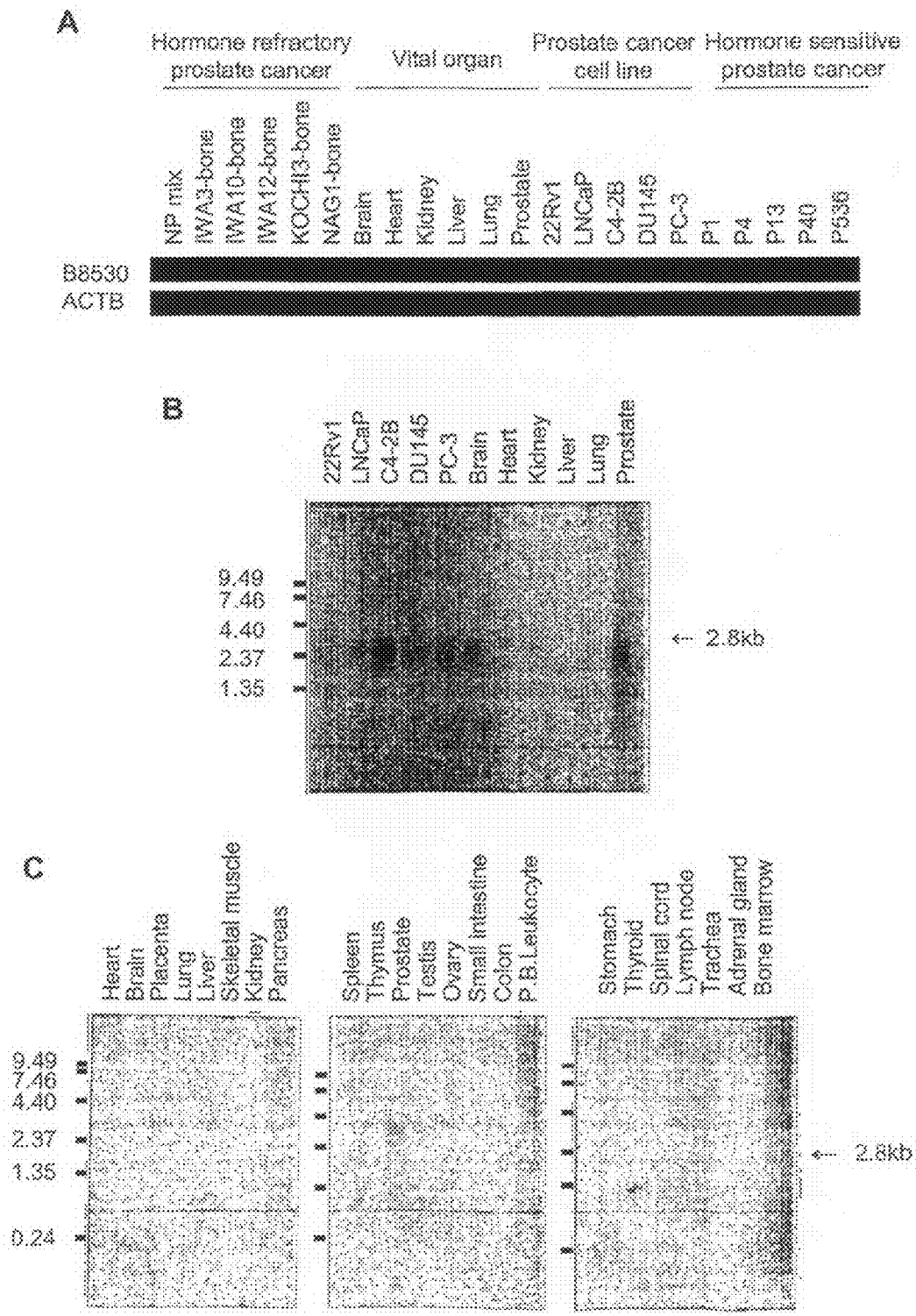
FIG. 1 shows the over-expression of STYK1 in hormone refractory prostate cancer (HRPC) cells. (A) Semi-quantitative RT-PCR verified up-regulated STYK1 expression in the microdissected HRPC cells compared with normal prostatic epithelial cell (NP mixture), which were also microdissected, and several vital organs (brain, heart, kidney, liver, lung, and prostate). Expression of ACTB served as the quantitative control. STYK1 over-expression was specifically observed in HRPC cells, but not in hormone sensitive prostate cancer cells. (B) Northern blot analysis showed strong expression of STYK1 in prostate cancer cell lines (22Rv, LNCaP, C4-2B, DU145, and PC-3), while only faint expression could be observed in adult normal brain and no expression at all in vital organs including heart, lung, liver, and kidney. (C) Multiple Tissues Northern (MTN) blot analysis showed faint expression of STYK1 only in normal prostate among various human normal adult organs.

The words "a", "an", and "the" as used herein mean "at least one" unless otherwise specifically indicated.

The terms "isolated" and "purified" used in relation with a substance (e.g., polypeptide, antibody, polynucleotide, etc.) indicates that the substance is substantially free from at least one substance that may else be included in the natural source. Thus, an isolated or purified antibody refers to antibodies that is substantially free of cellular material such as carbohydrate, lipid, or other contaminating proteins from the cell or tissue source from which the protein (antibody) is derived, or substantially free of chemical precursors or other chemicals when chemically synthesized. The term "substantially free of cellular material" includes preparations of a polypeptide in which the polypeptide is separated from cellular components of the cells from which it is isolated or recombinantly produced. Thus, a polypeptide that is substantially free of cellular material includes preparations of polypeptide having less than about 30%, 20%, 10%, or 5% (by dry weight) of heterologous protein (also referred to herein as a "contaminating protein"). When the polypeptide is recombinantly produced, it is also preferably substantially free of culture medium, which includes preparations of polypeptide with culture medium less than about 20%, 10%, or 5% of the volume of the protein preparation. When the polypeptide is produced by chemical synthesis, it is preferably substantially free of chemical precursors or other chemicals, which includes preparations of polypeptide with chemical precursors or other chemicals involved in the synthesis of the protein less than about 30%, 20%, 10%, 5% (by dry weight) of the volume of the protein preparation. That a particular protein preparation contains an isolated or purified polypeptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, antibodies and polypeptides of the present invention are isolated or purified. An "isolated" or "purified" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the present invention are isolated or purified.

The terms "polypeptide", "peptide", and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" refers to naturally occurring and synthetic amino acids, as well as amino acid analogs and amino acid mimetics that similarly functions to the naturally occurring amino acids. Naturally occurring amino acids are those encoded by the genetic code, as well as those modified after translation in cells (e.g., hydroxyproline, γ-carboxyglutamate, and O-phosphoserine). The phrase "amino acid analog" refers to compounds that have the same basic chemical structure (an a carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "polynucleotides", "oligonucleotide", "nucleotides", "nucleic acids", and "nucleic acid molecules" are used interchangeably unless otherwise specifically indicated and are similarly to the amino acids referred to by their commonly accepted single-letter codes. Similar to the amino acids, they encompass both naturally-occuring and non-naturally occurring nucleic acid polymers. The polynucleotide, oligonucleotide, nucleotides, nucleic acids, or nucleic acid molecules may be composed of DNA, RNA or a combination thereof.

As use herein, the term "double-stranded molecule" refers to a nucleic acid molecule that inhibits expression of a target gene including, for example, short interfering RNA (siRNA; e.g., double-stranded ribonucleic acid (dsRNA) or small hairpin RNA (shRNA)) and short interfering DNA/RNA (siD/R-NA; e.g. double-stranded chimera of DNA and RNA (dsD/R-NA) or small hairpin chimera of DNA and RNA (shD/R-NA)).

As used herein, the term "dsRNA" refers to a construct of two RNA molecules comprising complementary sequences to one another and that have annealed together via the complementary sequences to form a double-stranded RNA molecule. The nucleotide sequence of two strands may comprise not only the "sense" or "antisense" RNAs selected from a protein coding sequence of target gene sequence, but also RNA molecule having a nucleotide sequence selected from non-coding rigion of the target gene.

The term "shRNA", as used herein, refers to an siRNA having a stem-loop structure, comprising a first and second regions complementary to one another, i.e., sense and antisense strands. The degree of complementarity and orientation of the regions being sufficient such that base pairing occurs between the regions, the first and second regions being joined by a loop region, the loop resulting from a lack of base pairing between nucleotides (or nucleotide analogs) within the loop region. The loop region of an shRNA is a single-stranded region intervening between the sense and antisense strands and may also be referred to as "intervening single-strand".

As use herein, the term "siD/R-NA" refers to a double-stranded polynucleotide molecule which is composed of both RNA and DNA, and includes hybrids and chimeras of RNA and DNA and prevents translation of a target mRNA. Herein, a hybrid indicates a molecule wherein a polynucleotide composed of DNA and a polynucleotied composed of RNA hybridize to each other to form the double-stranded molecule; whereas a chimera indicates that one or both of the strands composing the double stranded molecule may contain RNA and DNA. Standard techniques of introducing siD/R-NA into the cell are used. The siD/R-NA includes a sense nucleic acid sequence (also referred to as "sense strand"), an antisense nucleic acid sequence (also referred to as "antisense strand") or both. The siD/R-NA may be constructed such that a single transcript has both the sense and complementary antisense nucleic acid sequences from the target gene, e.g., a hairpin. The siD/R-NA may either be a dsD/R-NA or shD/R-NA.

As used herein, the term "dsD/R-NA" refers to a construct of two molecules comprising complementary sequences to one another and that have annealed together via the complementary sequences to form a double-stranded polynucleotide molecule. The nucleotide sequence of two strands may comprise not only the "sense" or "antisense" polynucleotides sequence selected from a protein coding sequence of target gene sequence, but also polynucleotide having a nucleotide sequence selected from non-coding region of the target gene. One or both of the two molecules constructing the dsD/R-NA are composed of both RNA and DNA (chimeric molecule), or alternatively, one of the molecules is composed of RNA and the other is composed of DNA (hybrid double-strand).

The term "shD/R-NA", as used herein, refers to an siD/R-NA having a stem-loop structure, comprising a first and second regions complementary to one another, i.e., sense and antisense strands. The degree of complementarity and orientation of the regions being sufficient such that base pairing occurs between the regions, the first and second regions being joined by a loop region, the loop resulting from a lack of base pairing between nucleotides (or nucleotide analogs) within the loop region. The loop region of an shD/R-NA is a single-stranded region intervening between the sense and antisense strands and may also be referred to as "intervening single-strand".

The present invention is based in part on the discovery of elevated expression of the STYK1 gene in cells from patients of prostate cancers. The expression of the gene was discovered to be particularly elevated in hormone refractory prostate cancer (HRPC). The nucleotide sequence of human STYK1 gene is shown in SEQ ID NO: 8 and is also available as GenBank Accession No. NM_018423. Herein, the STYK1 gene encompasses the human STYK1 gene as well as those of other animals including non-human primate, mouse, rat, dog, cat, horse, and cow but are not limited thereto, and includes allelic mutants and genes found in other animals as corresponding to the STYK1 gene.

The amino acid sequence encoded the human STYK1 gene is shown in SEQ ID NO: 9 and is also available as GenBank Accession No. NP_060893.1. In the present invention, the polypeptide encoded by the STYK1 gene is referred to as "STYK1", and sometimes as "STYK1 polypeptide" or "STYK1 protein".

According to an aspect of the present invention, functional equivalents are also included in the STYK1 polypeptide. Herein, a "functional equivalent" of a protein is a polypeptide that has a biological activity equivalent to the protein.

Namely, any polypeptide that retains the biological ability of the STYK1 protein may be used as such a functional equivalent in the present invention. Such functional equivalents include those wherein one or more amino acids are substituted, deleted, added, or inserted to the natural occurring amino acid sequence of the STYK1 protein. Alternatively, the polypeptide may be one that comprises an amino acid sequence having at least about 80% homology (also referred to as sequence identity) to the sequence of the respective proteins. In other embodiments, the polypeptide can be encoded by a polynucleotide that hybridizes under stringent conditions to the natural occurring nucleotide sequence of the STYK1 gene.

The phrase "stringent (hybridization) conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes, "Overview of principles of hybridization and the strategy of nucleic acid assays"* (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times of background, preferably 10 times of background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 50° C.

Generally, it is known that modifications of one or more amino acid in a protein do not influence the function of the protein. One of skill in the art will recognize that individual additions, deletions, insertions, or substitutions to an amino acid sequence which alters a single amino acid or a small percentage of amino acids is a "conservative modification" wherein the alteration of a protein results in a protein with similar functions. Conservative substitution tables providing functionally similar amino acids are well known in the art. For example, the following eight groups each contain amino acids that are conservative substitutions for one another:

1) Alanine (A), Glycine (G);
2) Aspartic acid (d), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cystein (C), Methionine (M) (see, e.g., Creighton, *Proteins* 1984).

Such conservatively modified polypeptides are included in the present STYK1 protein. However, the present invention is not restricted thereto and the STYK1 protein includes nonconservative modifications so long as they retain at least one biological activity of the STYK1 protein. Furthermore, the modified proteins do not exclude polymorphic variants, interspecies homologues, and those encoded by alleles of these proteins.

Moreover, the STYK1 gene of the present invention encompasses polynucleotides that encode such functional equivalents of the STYK1 protein.

Unless otherwise defined, all technical and scientific terms used herein have the same meaning as commonly understood by one of ordinary skill in the art to which this invention belongs. In case of conflict, the present specification, including definitions, will control.

I. Diagnosing Cancer:
I-1. Method for Diagnosing Cancer or a Predisposition for Developing Cancer The expression of the STYK1 gene was found to be specifically elevated in patients with cancer, more particularly, in prostate cancer including HRPC. Therefore, the gene identified herein as well as its transcription and translation products find diagnostic utility as a marker for prostate cancer and by measuring the expression of the STYK1 gene in a cell sample, prostate cancer can be diagnosed. Specifically, the present invention provides a method for diagnosing cancer or a predisposition for developing cancer in a subject by determining the expression level of the STYK1 gene in the subject.

Preferable cancers to be diagnosed by the present method include prostate cancer, and more suitably is HRPC.

In the context of the present invention, the term "diagnosing" is intended to encompass predictions and likelihood analysis. The present method is intended to be used clinically in making decisions concerning treatment modalities, including therapeutic intervention, diagnostic criteria such as disease stages, and disease monitoring and surveillance for cancer. According to the present invention, an intermediate result for examining the condition of a subject may also be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

A subject to be diagnosed by the present method is preferably a mammal. Exemplary mammals include, but are not limited to, human, non-human primate, mouse, rat, dog, cat, horse, and cow.

It is preferred to collect a biological sample from the subject to be diagnosed to perform the diagnosis. Any biological material can be used as the biological sample for the determination so long as it comprises the objective transcription or translation product of the STYK1 gene. The biological samples include, but are not limited to, bodily tissues and fluids, such as blood, sputum, and urine. Preferably, the biological sample contains a cell population comprising an epithelial cell, more preferably a cancerous prostate epithelial cell or a prostate epithelial cell derived from tissue suspected to be cancerous. Further, if necessary, the cell may be purified from the obtained bodily tissues and fluids, and then used as the biological sample.

According to the present invention, the expression level of the STYK1 gene is determined in the subject-derived biological sample. The expression level can be determined at the transcription (nucleic acid) product level, using methods known in the art. For example, the mRNA of the STYK1 gene may be quantified using probes by hybridization methods (e.g., Northern hybridization). The detection may be carried out on a chip or an array. The use of an array is preferable for detecting the expression level of a plurality of genes (e.g., various cancer specific genes) including the present STYK1 gene. Those skilled in the art can prepare such probes utilizing the sequence information of the STYK1 gene (SEQ ID NO: 8; GenBank Accession No. NM_018423). For example, the cDNA of the STYK1 gene may be used as the probes. If necessary, the probe may be labeled with a suitable label, such as dyes and isotopes, and the expression level of the gene may be detected as the intensity of the hybridized labels.

Furthermore, the transcription product of the STYK1 gene may be quantified using primers by amplification-based detection methods (e.g., RT-PCR). Such primers can also be prepared based on the available sequence information of the gene. For example, the primers (SEQ ID NOs: 3 and 4) used in the Example may be employed for the detection by RT-PCR, but the present invention is not restricted thereto.

Specifically, a probe or primer used for the present method hybridizes under stringent, moderately stringent, or low stringent conditions to the mRNA of the STYK1 gene. As used herein, the phrase "stringent (hybridization) conditions" refers to conditions under which a probe or primer will hybridize to its target sequence, but to no other sequences. Stringent conditions are sequence-dependent and will be different under different circumstances. Specific hybridization of longer sequences is observed at higher temperatures than shorter sequences. Generally, the temperature of a stringent condition is selected to be about 5° C. lower than the thermal melting point ($T_m$) for a specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes or primers (e.g., 10 to 50 nucleotides) and at least about 60° C. for longer probes or primers. Stringent conditions may also be achieved with the addition of destabilizing agents, such as formamide.

Alternatively, the translation product may be detected for the diagnosis of the present invention. For example, the quantity of the STYK1 protein may be determined. A method for determining the quantity of the protein as the translation product includes immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment retains the binding ability to the STYK1 protein. Methods to prepare these kinds of antibodies for the detection of proteins are well known in the art (e.g., see EXAMPLE I), and any method may be employed in the present invention to prepare such antibodies and equivalents thereof.

As another method to detect the expression level of the STYK1 gene based on its translation product, the intensity of staining may be observed via immunohistochemical analysis using an antibody against the STYK1 protein. Namely, the observation of strong staining indicates increased presence of the protein and at the same time high expression level of the STYK1 gene.

Furthermore, the translation product may be detected based on its biological activity. Specifically, the STYK1 protein has been known to have kinase activity (Ye X, et al., *Mol Biol Rep* 2003, 30(2): 91-6; Liu L, et al., *Cancer Res* 2004, 64(10): 3491-9), and was demonstrated herein to be involved in the migration of cancer cells. Thus, kinase activity or the cancer cell growth promoting ability of the STYK1 protein may be used as an index of the STYK1 protein existing in the biological sample.

Moreover, in addition to the expression level of the STYK1 gene, the expression level of other cancer-associated genes, for example, genes known to be differentially expressed in HRPC, may also be determined to improve the accuracy of the diagnosis.

The expression level of cancer marker gene including the STYK1 gene in a biological sample can be considered to be increased if it increases from the control level of the corresponding cancer marker gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the test biological sample by using a sample(s) previously collected and stored from a subject/subjects whose disease state (cancerous or non-cancerous) is/are known. Alternatively, the control level may be determined by a statistical method based on the results obtained by analyzing previously determined expression level(s) of the STYK1 gene in samples from subjects whose disease state are known. Furthermore, the control level can be a database of expression patterns from previously tested cells. Moreover, according to an aspect of the present invention, the expression level of the STYK1 gene in a biological sample may be compared to multiple control levels, which control levels are determined from multiple reference samples. It is preferred to use a control level determined from a reference sample derived from a tissue type similar to that of the patient-derived biological sample. Moreover, it is preferred, to use the standard value of the expression levels of the STYK1 gene in a population with a known disease state. The standard value may be obtained by any method known in the art. For example, a range of mean±2 S.D. or mean±3 S.D. may be used as standard value.

In the context of the present invention, a control level determined from a biological sample that is known not to be cancerous is called "normal control level". On the other hand, if the control level is determined from a cancerous biological sample, it will be called "cancerous control level".

When the expression level of the STYK1 gene is increased compared to the normal control level or is similar to the cancerous control level, the subject may be diagnosed to be suffering from or at a risk of developing cancer. Furthermore, in case where the expression levels of multiple cancer-related genes are compare, a similarity in the gene expression pattern between the sample and the reference which is cancerous indicates that the subject is suffering from or at a risk of developing cancer.

Difference between the expression levels of a test biological sample and the control level can be normalized to the expression level of control nucleic acids, e.g. housekeeping genes. Genes whose expression levels are known not to differ depending on the cancerous or non-cancerous state of the cell. Exemplary control genes include, but are not limited to, β-actin, glyceraldehyde 3-phosphate dehydrogenase, and ribosomal protein P1.

I-2. Assessing Efficacy of Cancer Treatment

The STYK1 gene differentially expressed between normal and cancerous cells also allow for the course of treatment of cancers to be monitored, and the above-described method for diagnosing cancer can be applied for assessing the efficacy of a treatment on cancer. Specifically, the efficacy of a treatment on cancer can be assessed by determining the expression level of the STYK1 gene in a cell(s) derived from a subject undergoing the treatment. If desired, test cell populations are obtained from the subject at various time points, before, during, and/or after the treatment. The expression level of the STYK1 gene can be, for example, determined following the method described above under the item of 'I-1. Method for diagnosing cancer or a predisposition for developing cancer'. In the context of the present invention, it is preferred that the control level to which the detected expression level is compared is determined from the STYK1 gene expression in a cell(s) not exposed to the treatment of interest.

If the expression level of the STYK1 gene is compared to a control level that is determined from a normal cell or a cell population containing no cancer cell, a similarity in the expression level indicates that the treatment of interest is efficacious and a difference in the expression level indicates less favorable clinical outcome or prognosis of that treatment. On the other hand, if the comparison is conducted against a control level that is determined from a cancer cell or a cell population containing a cancer cell(s), a difference in the expression level indicates efficacious treatment, while a similarity in the expression level indicates less favorable clinical outcome or prognosis.

Furthermore, the expression levels of the STYK1 gene before and after a treatment can be compared according to the present method to assess the efficacy of the treatment. Specifically, the expression level detected in a subject-derived biological sample after a treatment (i.e., post-treatment level) is compared to the expression level detected in a biological sample obtained prior to treatment onset from the same subject (i.e., pre-treatment level). A decrease in the post-treatment level compared to the pre-treatment level indicates that the treatment of interest is efficacious while an increase in or similarity of the post-treatment level to the pre-treatment level indicates less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of carcinoma in a subject. When a treatment of interest is applied prophylactically, "efficacious" means that the treatment retards or prevents the forming of tumor or retards, prevents, or alleviates at least one clinical symptom of cancer. Assessment of the state of tumor in a subject can be made using standard clinical protocols.

In addition, efficaciousness of a treatment can be determined in association with any known method for diagnosing cancer. Cancers can be diagnosed, for example, by identifying symptomatic anomalies, e.g., weight loss, abdominal pain, back pain, anorexia, nausea, vomiting and generalized malaise, weakness, and jaundice.

I-3. Assessing Prognosis of Subject with Cancer

The method for diagnosing cancer described above can also be used for assessing the prognosis of cancer in a subject. Thus, the present invention also provides a method for assessing the prognosis of a subject with cancer. The expression level of the STYK1 gene can be, for example, determined following the method described above under the item of 'I-1. Method for diagnosing cancer or a predisposition for developing cancer'. For example, the expression level of the STYK1 gene in biological samples derived from patients over a spectrum of disease stages can be used as control levels to be compared with the expression level of the gene detected for a subject. By comparing the expression level of the STYK1 gene in a subject and the control level(s) the prognosis of the subject can be assessed. Alternatively, by comparing over time the pattern of expression levels in a subject, the prognosis of the subject can be assessed.

For example, an increase in the expression level of STYK1 gene in a subject as compared to a normal control level indicates less favorable prognosis. Conversely, a similarity in the expression level as compared to normal control level indicates a more favorable prognosis for the subject.

II. Kits:

The present invention also provides reagents for detecting cancer, i.e., reagents that can detect the transcription or translation product of the STYK1 gene. Specifically, such reagents include nucleic acids that specifically bind to or identify a transcription product of the STYK1 gene. For example, the nucleic acid that specifically bind to or identify a transcription product of the STYK1 gene include such as oligonucleotides (e.g., probes and primers) having a sequence that is complementary to a portion of the STYK1 gene transcription product. Alternatively, antibodies can be exemplified as reagents for detecting the translation product of the gene. The probes, primers, and antibodies described above under the item of 'I-1. Method for diagnosing cancer or a predisposition for developing cancer' can be mentioned as suitable examples of such reagents.

The translation product may also be detected based on its biological activity. According to the human Kinome Map (www.cellsignal.com/reference/kinase/kinome.html), STYK1 gene is mapped at the trunk of the tyrosine kinase branch (Manning C, et al. *Science* 2002, 298: 1912-34). Thus, the kinase activity of the STYK1 protein may be detected for determining the expression level of the STYK1 gene. For example, labeled substrate(s) of the STYK1 protein may be used as a reagent for detecting the expression level of the gene. Thus, according to an aspect of the present invention, a kit for detecting the expression of the STYK1 gene may comprise a labeled substrate of the STYK1 protein.

The present kit is suited for detecting prostate cancer, more suitably HRPC.

These reagents may be used for the above-described diagnosis of cancer. The assay format for using the reagents may be Northern hybridization or sandwich ELISA, both of which are well-known in the art.

The detection reagents may be packaged together in the form of a kit. For example, the detection reagents may be packaged in separate containers. Furthermore, the detection reagents may be packaged with other reagents necessary for the detection. For example a kit may include a nucleic acid or antibody (either bound to a solid matrix or packaged separately with reagents for binding them to the matrix) as the detection reagent, a control reagent (positive and/or negative), and/or a detectable label. Instructions (e.g., written, tape, VCR, CD-ROM, etc.) for carrying out the assay may also be included in the kit.

As an aspect of the present invention, the reagents for detecting cancer may be immobilized on a solid matrix, such as a porous strip, to form at least one site for detecting cancer. The measurement or detection region of the porous strip may include a plurality of sites, each containing a detection reagent (e.g., nucleic acid). A test strip may also contain sites for negative and/or positive controls. Alternatively, control sites may be located on a separate strip from the test strip. Optionally, the different detection sites may contain different amounts of immobilized detection reagents (e.g., nucleic acid), i.e., a higher amount in the first detection site and lesser amounts in subsequent sites. Upon the addition of test biological sample, the number of sites displaying a detectable signal provides a quantitative indication of the expression level of the STYK1 gene in the sample. The detection sites may be configured in any suitably detectable shape and are typically in the shape of a bar or dot spanning the width of a test strip.

III. Screening Methods:

Using the STYK1 gene, polypeptides encoded by the gene or fragments thereof, or transcriptional regulatory region of the gene, it is possible to screen agents that alter the expression of the gene or the biological activity of a polypeptide encoded by the gene. Such agents can be used as pharmaceuticals for treating or preventing cancer, in particular, prostate cancer (e.g., HRPC). Thus, the present invention provides methods of screening for agents for treating or preventing cancer using the STYK1 gene, polypeptid encoded by the gene or fragments thereof, or transcriptional regulatory region of the gene.

An agent isolated by the screening method of the present invention is an agent that is expected to inhibit the expression of the STYK1 gene or the activity of the translation product of the gene, and thus, is a candidate for treating or preventing diseases attributed to, for example, cell proliferative diseases, such as cancer (in particular, prostate cancer). The agents are expected to be particularly suited for the treatment or prevention of HRPC. Namely, the agents screened through the present methods are deemed to have a clinical benefit and can be further tested for its ability to prevent cancer cell growth in animal models or test subjects.

In the context of the present invention, agents to be identified through the present screening methods may be any compound or composition including several compounds. Furthermore, the test agent exposed to a cell or protein according to the screening methods of the present invention may be a single compound or a combination of compounds. When a combination of compounds is used in the methods, the compounds may be contacted sequentially or simultaneously.

Any test agent, for example, cell extracts, cell culture supernatant, products of fermenting microorganism, extracts from marine organism, plant extracts, purified or crude proteins, peptides, non-peptide compounds, synthetic micromolecular compounds (including nucleic acid constructs, such as antisense RNA, siRNA, Ribozymes, etc.) and natural compounds can be used in the screening methods of the present invention. The test agent of the present invention can be also obtained using any of the numerous approaches in combinatorial library methods known in the art, including (1) biological libraries,
(2) spatially addressable parallel solid phase or solution phase libraries,
(3) synthetic library methods requiring deconvolution,
(4) the "one-bead one-compound" library method and
(5) synthetic library methods using affinity chromatography selection.

The biological library methods using affinity chromatography selection is limited to peptide libraries, while the other four approaches are applicable to peptide, non-peptide oligomer or small molecule libraries of compounds (Lam, *Anticancer Drug Des* 1997, 12: 145-67). Examples of methods for the synthesis of molecular libraries can be found in the art (DeWitt et al., *Proc Natl Acad Sci USA* 1993, 90: 6909-13; Erb et al., *Proc Natl Acad Sci USA* 1994, 91: 11422-6; Zuckermann et al., *J Med Chem* 37: 2678-85, 1994; Cho et al., *Science* 1993, 261: 1303-5; Carell et al., *Angew Chem Int Ed Engl* 1994, 33: 2059; Carell et al., *Angew Chem Int Ed Engl* 1994, 33: 2061; Gallop et al., *J Med Chem* 1994, 37: 1233-51). Libraries of compounds may be presented in solution (see Houghten, *Bio/Techniques* 1992, 13: 412-21) or on beads (Lam, *Nature* 1991, 354: 82-4), chips (Fodor, *Nature* 1993, 364: 555-6), bacteria (U.S. Pat. No. 5,223,409), spores (U.S. Pat. Nos. 5,571,698, 5,403,484, and 5,223,409), plasmids (Cull et al., *Proc Natl Acad Sci USA* 1992, 89: 1865-9) or phage (Scott and Smith, *Science* 1990, 249: 386-90; Devlin, *Science* 1990, 249: 404-6; Cwirla et al., *Proc Natl Acad Sci USA* 1990, 87: 6378-82; Felici, *J Mol Biol* 1991, 222: 301-10; US Pat. Application 2002103360).

A compound in which a part of the structure of the compound screened by any of the present screening methods is converted by addition, deletion and/or replacement, is included in the agents obtained by the screening methods of the present invention.

Furthermore, when the screened test agent is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA find use in preparing the test agent which is a candidate for treating or preventing cancer.

III-1. Protein Based Screening Methods

According to the present invention, the expression of the STYK1 gene was suggested to be crucial for the growth and/or survival of cancer cells, in particular prostate cancer cells (e.g., HRPC cells). Therefore, it was considered that agents which suppress the function of the polypeptide encoded by the gene inhibit the growth and/or survival of cancer cells, and find use in treating or preventing cancer. Thus, the present invention provides methods of screening an agent for treating or preventing cancer, using the STYK1 polypeptide.

In addition to the STYK1 polypeptide, fragments of the polypeptide may be used for the present screening so long as it retains at least one biological activity of the natural occurring STYK1 polypeptide.

The polypeptide or fragments thereof may be further linked to other substances so long as the polypeptide and fragments retains at least one of its biological activity. Usable substances include: peptides, lipids, sugar and sugar chains, acetyl groups, natural and synthetic polymers, etc. These kinds of modifications may be performed to confer additional functions or to stabilize the polypeptide and fragments.

The polypeptide or fragments used for the present method may be obtained from nature as naturally occurring proteins via conventional purification methods or through chemical synthesis based on the selected amino acid sequence. For example, conventional peptide synthesis methods that can be adopted for the synthesis include:

1) *Peptide Synthesis,* Interscience, New York, 1966;
2) *The Proteins,* Vol. 2, Academic Press, New York, 1976;
3) *Peptide Synthesis* (in Japanese), Maruzen Co., 1975;
4) *Basics and Experiment of Peptide Synthesis* (in Japanese), Maruzen Co., 1985;
5) *Development of Pharmaceuticals* (second volume) (in Japanese), Vol. 14 (peptide synthesis), Hirokawa, 1991;
6) WO99/67288; and
7) Barany G. & Merrifield R. B., *Peptides* Vol. 2, "Solid Phase Peptide Synthesis", Academic Press, New York, 1980, 100-118.

Alternatively, the protein may be obtained adopting any known genetic engineering methods for producing polypeptides (e.g., Morrison J., *J Bacteriology* 1977, 132: 349-51; Clark-Curtiss & Curtiss, *Methods in Enzymology* (eds. Wu et al.) 1983, 101: 347-62). For example, first, a suitable vector comprising a polynucleotide encoding the objective protein in an expressible form (e.g., downstream of a regulatory sequence comprising a promoter) is prepared, transformed into a suitable host cell, and then the host cell is cultured to produce the protein. More specifically, a gene encoding the STYK1 polypeptide is expressed in host (e.g., animal) cells and such by inserting the gene into a vector for expressing foreign genes, such as pSV2neo, pcDNA I, pcDNA3.1, pCAGGS, or pCD8. A promoter may be used for the expression. Any commonly used promoters may be employed including, for example, the SV40 early promoter (Rigby in Williamson (ed.), *Genetic Engineering*, vol. 3. Academic Press, London, 1982, 83-141), the EF-α promoter (Kim et al., *Gene* 1990, 91:217-23), the CAG promoter (Niwa et al., *Gene* 1991, 108:193), the RSV LTR promoter (Cullen, *Methods in Enzymology* 1987, 152:684-704), the SRα promoter (Takebe et al., *Mol Cell Biol* 1988, 8:466), the CMV immediate early promoter (Seed et al., *Proc Natl Acad Sci USA* 1987, 84:3365-9), the SV40 late promoter (Gheysen et al., *J Mol Appl Genet* 1982, 1:385-94), the Adenovirus late promoter (Kaufman et al., *Mol Cell Biol* 1989, 9:946), the HSV TK promoter, and such. The introduction of the vector into host cells to express the STYK1 gene can be performed according to any methods, for example, the electroporation method (Chu et al., *Nucleic Acids Res* 1987, 15:1311-26), the calcium phosphate method (Chen et al., *Mol Cell Biol* 1987, 7:2745-52), the DEAE dextran method (Lopata et al., *Nucleic Acids Res* 1984, 12:5707-17; Sussman et al., *Mol Cell Biol* 1985, 4:1641-3), the Lipofectin method (Derijard B, *Cell* 1994, 7:1025-37; Lamb et al., *Nature Genetics* 1993, 5:22-30; Rabindran et al., *Science* 1993, 259:230-4), and such.

The STYK1 protein may also be produced in vitro adopting an in vitro translation system.

The STYK1 polypeptide to be contacted with a test agent can be, for example, a purified polypeptide, a soluble protein, or a fusion protein fused with other polypeptides.

III-1-1. Identifying Agents that Bind to STYK1 Polypeptide

An agent that binds to a protein is likely to alter the expression of the gene coding for the protein or the biological activity of the protein. Thus, as an aspect, the present invention provides a method of screening an agent for treating or preventing cancer, which comprises the steps of:
a) contacting a test agent with the STYK1 polypeptide or a fragment thereof;
b) detecting the binding between the polypeptide or fragment and the test agent; and
c) selecting the test agent that binds to the polypeptide as a candidate agent for treating or preventing cancer.

The binding of a test agent to the STYK1 polypeptide may be, for example, detected by immunoprecipitation using an antibody against the polypeptide. Therefore, for the purpose for such detection, it is preferred that the STYK1 polypeptide or fragments thereof used for the screening contains an antibody recognition site. The antibody used for the screening may be one that recognizes an antigenic region (e.g., epitope) of the present STYK1 polypeptide which preparation methods are well known in the art, and any method may be employed in the present invention to prepare such antibodies and equivalents thereof.

Alternatively, the STYK1 polypeptide or a fragment thereof may be expressed as a fusion protein comprising at its N- or C-terminus a recognition site (epitope) of a monoclonal antibody, whose specificity has been revealed, to the N- or C-terminus of the polypeptide. A commercially available epitope-antibody system can be used (*Experimental Medicine* 1995, 13:85-90). Vectors which can express a fusion protein with, for example, β-galactosidase, maltose binding protein, glutathione S-transferase, green florescence protein (GFP), and such by the use of its multiple cloning sites are commercially available and can be used for the present invention. Furthermore, fusion proteins containing much smaller epitopes to be detected by immunoprecipitation with an antibody against the epitopes are also known in the art (*Experimental Medicine* 1995, 13:85-90). Such epitopes consisting of several to a dozen amino acids so as not to change the property of the STYK1 polypeptide or fragments thereof can also be used in the present invention. Examples include polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such.

Glutathione S-transferase (GST) is also well-known as the counterpart of the fusion protein to be detected by immunoprecipitation. When GST is used as the protein to be fused with the STYK1 polypeptide or fragment thereof to form a fusion protein, the fusion protein can be detected either with an antibody against GST or a substance specifically binding to GST, i.e., such as glutathione (e.g., glutathione-Sepharose 4B).

In immunoprecipitation, an immune complex is formed by adding an antibody (recognizing the STYK1 polypeptide or a fragment thereof itself, or an epitope tagged to the polypeptide or fragment) to the reaction mixture of the STYK1 polypeptide and the test agent. If the test agent has the ability to bind the polypeptide, then the formed immune complex will consists of the STYK1 polypeptide, the test agent, and the antibody. On the contrary, if the test agent is devoid of such ability, then the formed immune complex only consists of the STYK1 polypeptide and the antibody. Therefore, the binding ability of a test agent to STYK1 polypeptide can be examined by, for example, measuring the size of the formed immune complex. Any method for detecting the size of a substance can be used, including chromatography, electrophoresis, and such. For example, when mouse IgG antibody is used for the detection, Protein A or Protein G sepharose can be used for quantitating the formed immune complex.

For more details on immunoprecipitation see, for example, Harlow et al., *Antibodies*, Cold Spring Harbor Laboratory publications, New York, 1988, 511-52.

Furthermore, the STYK1 polypeptide or a fragment thereof used for the screening of agents that bind to thereto may be bound to a carrier. Example of carriers that may be used for binding the polypeptides include insoluble polysaccharides, such as agarose, cellulose and dextran; and synthetic resins, such as polyacrylamide, polystyrene and silicon; preferably commercially available beads and plates (e.g., multi-well plates, biosensor chip, etc.) prepared from the above materials may be used. When using beads, they may be filled into a column. Alternatively, the use of magnetic beads is also known in the art, and enables to readily isolate polypeptides and agents bound on the beads via magnetism.

The binding of a polypeptide to a carrier may be conducted according to routine methods, such as chemical bonding and physical adsorption. Alternatively, a polypeptide may be bound to a carrier via antibodies specifically recognizing the protein. Moreover, binding of a polypeptide to a carrier can also be conducted by means of interacting molecules, such as the combination of avidin and biotin.

Screening using such carrier-bound STYK1 polypeptide or fragments thereof include, for example, contacting a test agent to the carrier-bound polypeptide, incubating the mixture, washing the carrier, and detecting and/or measuring the agent bound to the carrier. The binding may be carried out in buffer, for example, but are not limited to, phosphate buffer and Tris buffer, as long as the buffer does not inhibit the binding.

A screening method wherein such carrier-bound STYK1 polypeptide or fragments thereof and a composition (e.g., cell extracts, cell lysates, etc.) are used as the test agent, such method is generally called affinity chromatography. For example, the STYK1 polypeptide may be immobilized on a carrier of an affinity column, and a test agent, containing a substance capable of binding to the polypeptides, is applied to the column. After loading the test agent, the column is washed, and then the substance bound to the polypeptide is eluted with an appropriate buffer.

A biosensor using the surface plasmon resonance phenomenon may be used as a mean for detecting or quantifying the bound agent in the present invention. When such a biosensor is used, the interaction between the STYK1 polypeptide and a test agent can be observed real-time as a surface plasmon resonance signal, using only a minute amount of the polypeptide and without labeling (for example, BIAcore, Pharmacia). Therefore, it is possible to evaluate the binding between the polypeptide and test agent using a biosensor such as BIAcore.

Methods of screening for molecules that bind to a specific protein among synthetic chemical compounds, or molecules in natural substance banks or a random phage peptide display library by exposing the specific protein immobilized on a carrier to the molecules, and methods of high-throughput screening based on combinatorial chemistry techniques (Wrighton et al., *Science* 1996, 273:458-64; Verdine, *Nature* 1996, 384:11-3) to isolate not only proteins but chemical compounds are also well-known to those skilled in the art. These methods can also be used for screening agents (including agonist and antagonist) that bind to the STYK1 protein or fragments thereof.

When the test agent is a protein, for example, West-Western blotting analysis (Skolnik et al., *Cell* 1991, 65:83-90) can be used for the present method. Specifically, a protein binding to the STYK1 polypeptide can be obtained by preparing first a cDNA library from cells, tissues, organs, or cultured cells (e.g., PC cell lines) expected to express at least one protein binding to the STYK1 polypeptide using a phage vector (e.g., ZAP), expressing the proteins encoded by the vectors of the cDNA library on LB-agarose, fixing the expressed proteins on a filter, reacting the purified and labeled STYK1 polypeptide with the above filter, and detecting the plaques expressing proteins to which the STYK1 polypeptide has bound according to the label of the STYK1 polypeptide.

Labeling substances such as radioisotope (e.g., $^{3}$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiocyanate (FITC), rhodamine) and biotin/avidin, may be used for the labeling of STYK1 polypeptide in the present method. When the protein is labeled with radioisotope, the detection or measurement can be carried out by liquid scintillation. Alternatively, when the protein is labeled with an enzyme, it can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Moreover, the STYK1 polypeptide bound to the protein can be detected or measured by utilizing an antibody that specifically binds to the STYK1 polypeptide, or a peptide or polypeptide (for example, GST) that is fused to the STYK1 polypeptide. In case of using an antibody in the present screening, the antibody is preferably labeled with one of the labeling substances mentioned above, and detected or measured based on the labeling substance. Alternatively, the antibody against the STYK1 polypeptide may be used as a primary antibody to be detected with a secondary antibody that is labeled with a labeling substance. Furthermore, the antibody bound to the STYK1 polypeptide in the present screening may be detected or measured using protein G or protein A column.

Alternatively, in another embodiment of the screening method of the present invention, two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton et al., *Cell* 1992, 68:597-612" and "Fields et al., *Trends Genet* 1994, 10:286-92"). In two-hybrid system, STYK1 polypeptide or a fragment thereof is fused to the SRF-binding region or GAL4-binding region and expressed in yeast cells. A cDNA library is prepared from cells expected to express at least one protein binding to the STYK1 polypeptide, such that the library, when expressed, is fused to the VP16 or GAL4 transcriptional activation region. The cDNA library is then introduced into the above yeast cells and the cDNA derived from the library is isolated from the positive clones detected (when a protein binding to the STYK1 polypeptide is expressed in the yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene and such can be used in addition to the HIS3 gene.

The agent isolated by this screening is a candidate for agonists or antagonists of the STYK1 polypeptide. The term "agonist" refers to molecules that activate the function of the polypeptide by binding thereto. On the other hand, the term "antagonist" refers to molecules that inhibit the function of the polypeptide by binding thereto. Moreover, an agent isolated by this screening as an antagonist is a candidate that inhibits the in vivo interaction of the STYK1 polypeptide with molecules (including nucleic acids (RNAs and DNAs) and proteins (e.g., the substrate phosphorylated by the STYK1 polypeptide)).

III-1-2. Identifying Agents by Detecting Biological Activity of the STYK1 Polypeptide According to the present invention, the expression of STYK1 gene was shown to be crucial for the growth and/or survival of cancer cells, in particular, prostate cancer cells (e.g., HRPC cells). Therefore, agents that suppress or inhibit the biological function of the translational product of the STYK1 gene is considered to serve as candidates for treating or preventing cancer. Thus, the present invention also provides a method for screening a compound for treating or preventing cancer using the STYK1 polypeptide or fragments thereof comprising the steps as follows:

a) contacting a test agent with the STYK1 polypeptide or a fragment thereof; and
b) detecting the biological activity of the polypeptide or fragment of step (a).

Any polypeptide can be used for the screening so long as it has one biological activity of the STYK1 polypeptide that can be used as an index in the present screening method. According to the present invention, the STYK1 polypeptide has been demonstrated to be required for the growth or viability of prostate cancer cells (more specifically, HRPC cells). Furthermore, the STYK1 gene is mapped at the trunk of the tyrosine kinase branch (Manning C et al., Science 2002, 298: 1912-34). Therefore, biological activities of the STYK1 polypeptide that can be used as an index for the screening include such cell growth promoting activity and kinase activity of the human STYK1 polypeptide. For example, a human STYK1 polypeptide can be used and polypeptides functionally equivalent thereto including fragments thereof can also be used. Such polypeptides may be expressed endogenously or exogenously by suitable cells.

When the biological activity to be detected in the present method is cell proliferation, it can be detected, for example, by preparing cells which express the STYK1 polypeptide or a fragment thereof (e.g., 22Rv1, C4-2B, P13, etc.), culturing the cells in the presence of a test agent, and determining the speed of cell proliferation, measuring the cell cycle and such, as well as by detecting wound-healing activity, conducting Matrigel invasion assay and measuring the colony forming activity.

According to an aspect of the present invention, the screening further comprises after the above step (b) the steps of:
  c) comparing the biological activity of the polypeptide or fragment with the biological activity detected in the absence of the agent; and
  d) selecting the agent that suppresses the biological activity of the polypeptide as a candidate agent for treating or preventing prostate cancer.

The agent isolated by this screening is a candidate for an antagonist of the STYK1 polypeptide, and thus, is a candidate that inhibits the in vivo interaction of the polypeptide with molecules (including nucleic acids (RNAs and DNAs) and proteins (e.g., the substrate phosphorylated by the STYK1 polypeptide)).

Herein, it was revealed that STYK1 polypeptide has kinase activity. Accordingly, an agent which decreases the kinase activity, i.e., one of the biological activity of STYK1 polypeptide may be used for treating or preventing cancer. Therefore the present invention further provides a method for screening an agent for treating or preventing cancer. An embodiment of this screening method comprises the steps of:
  (a) contacting a cell that expresses the STYK1 polypeptide or a fragment thereof with an agent;
  (b) detecting the kinase activity of the STYK1 polypeptide;
  (c) comparing the kinase activity of the STYK1 polypeptide with the kinase activity of the STYK1 polypeptide detected in the absence of the agent; and
  (d) selecting the agent that reduced the kinase activity of the STYK1 polypeptide as a candidate agent for treating or preventing cancer.

The kinase substrate of STYK1 can be readily identified by using commercially available kits for identifying the substrate involved in kinase activity. Examples of such kits include Serine/Threonine Kinase Substrate Screening Kit (Cell Signaling Technology, Inc), ProtoArray™ Human Kinase Substrate Identification Kit (Invitrogen), Kinase-Glo® Plus Luminescent Kinase Assay(a) (Promega), and such.

By using these kits, the STYK1 substrate may be identified by first reacting STYK1 with a microarray-like plate spotted with substrate-candidate proteins, and then detecting the spot on the plate that is phosphorylated by antibodies specific to phosphoric acid. The thus identified substrates can be used in the method of screening for compounds that inhibit the phosphorylation of the substrate by STYK1. According to this screening method, candidate compounds for suppressing the growth of prostate cancer cells, especially HRPC, can be identified.

The kinase activity of proteins are frequently reported to be involved in the mechanism of oncogenic transformation (e.g., HER2/neu and STI-571). For example, clinical trials using antibodies against HER2/neu and STI-571, which antibodies suppresses the kinase activity of these proteins, have proven these antibodies successful as pharmaceutical agents for treating cancer.

III-2. Nucleotide Based Screening Methods
III-2-1. Screening Method Using STYK1 Gene As discussed in detail above, by controlling the expression level of the STYK1 gene, one can control the onset and progression of cancer. Thus, agents that may be used in the treatment or prevention of cancers can be identified through screenings that use the expression levels of STYK1 gene as indices. In the context of the present invention, such screening may comprise, for example, the following steps:
  a) contacting a test agent with a cell expressing the STYK1 gene;
  b) detecting the expression level of the STYK1 gene;
  c) comparing the expression level with the expression level detected in the absence of the agent; and
  d) selecting the agent that reduces the expression level as a candidate agent for treating or preventing cancer.

An agent that inhibits the expression of the STYK1 gene or the activity of its gene product can be identified by contacting a cell expressing the STYK1 gene with a test agent and then determining the expression level of the STYK1 gene. Naturally, the identification may also be performed using a population of cells that express the gene in place of a single cell. A decreased expression level detected in the presence of an agent as compared to the expression level in the absence of the agent indicates the agent as being an inhibitor of the STYK1 gene, suggesting the possibility that the agent is useful for inhibiting cancer, thus a candidate agent to be used for the treatment or prevention of cancer.

The expression level of a gene can be estimated by methods well known to one skilled in the art. The expression level of the STYK1 gene can be, for example, determined following the method described above under the item of 'I-1. Method for diagnosing cancer or a predisposition for developing cancer'.

The cell or the cell population used for such identification may be any cell or any population of cells so long as it expresses the STYK1 gene. For example, the cell or population may be or contain a prostate epithelial cell derived from a tissue. Alternatively, the cell or population may be or contain an immortalized cell derived from a carcinoma cell, including HRPC cell. Cells expressing the STYK1 gene include, for example, cell lines established from cancers (e.g., PC cell lines such as 22Rv1, C4-2B, P13, etc.). Furthermore, the cell or population may be or contain a cell which has been transfected with the STYK1 gene.

The present method allows screening of various agents mentioned above and is particularly suited for screening functional nucleic acid molecules including antisense RNA, siRNA, and such.

III-2-2. Screening Method Using Transcriptional Regulatory Region of STYK1 Gene

According to another aspect, the present invention provides a method which comprises the following steps of:
  a) contacting a test agent with a cell into which a vector, comprising the transcriptional regulatory region of the STYK1 gene and a reporter gene that is expressed under the control of the transcriptional regulatory region, has been introduced;
  b) detecting the expression or activity of said reporter gene;

c) comparing the expression level or activity with the expression level or activity detected in the absence of the agent; and d) selecting the agent that reduces the expression or activity of said reporter gene as a candidate agent for treating or preventing cancer.

Suitable reporter genes and host cells are well known in the art. The reporter construct required for the screening can be prepared using the transcriptional regulatory region of the STYK1 gene, which can be obtained as a nucleotide segment containing the transcriptional regulatory region from a genome library based on the nucleotide sequence information of the gene.

The transcriptional regulatory region may be, for example, the promoter sequence of the STYK1 gene.

When a cell(s) transfected with a reporter gene that is operably linked to the regulatory sequence (e.g., promoter sequence) of the STYK1 gene is used, an agent can be identified as inhibiting or enhancing the expression of the STYK1 gene through detecting the expression level of the reporter gene product.

As a reporter gene, for example, Ade2 gene, lacZ gene, CAT gene, luciferase gene, HIS3 gene, and such well-known in the art can be used. Methods for detection of the expression of these genes are well known in the art.

III-3. Selecting Therapeutic Agents that are Appropriate for a Particular Individual Differences in the genetic makeup of individuals can result in differences in their relative abilities to metabolize various drugs. An agent that is metabolized in a subject to act as an anti-tumor agent can manifest itself by inducing a change in a gene expression pattern in the subject's cells from that characteristic of a cancerous state to a gene expression pattern characteristic of a non-cancerous state. Accordingly, the STYK1 gene differentially expressed between cancerous and non-cancerous cells disclosed herein allow for a putative therapeutic or prophylactic inhibitor of cancer to be tested in a test cell population from a selected subject in order to determine if the agent is a suitable inhibitor of cancer in the subject.

To identify an inhibitor of cancer that is appropriate for a specific subject, a test cell population from the subject is exposed to a candidate therapeutic agent, and the expression of STYK1 gene is determined.

In the context of the method of the present invention, test cell populations contain cancer cells expressing the STYK1 gene. Preferably, the test cell is a prostate epithelial cell.

Specifically, a test cell population may be incubated in the presence of a candidate therapeutic agent and the expression of the STYK1 gene in the test cell population may be measured and compared to one or more reference profiles, e.g., a cancerous reference expression profile or a non-cancerous reference expression profile.

A decrease in the expression of the STYK1 gene in a test cell population relative to a reference cell population containing cancer indicates that the agent has therapeutic potential. Alternatively, a similarity in the expression of the STYK1 gene in a test cell population relative to a reference cell population not containing cancer indicates that the agent has therapeutic potential.

IV. Pharmaceutical Compositions for Treaties or Preventing Cancer:

The agents screened by any of the screening methods of the present invention, antisense nucleic acids and siRNAs of the STYK1 gene, and antibodies against the STYK1 polypeptide inhibit or suppress the expression of the STYK1 gene, or the biological activity of the STYK1 polypeptide and inhibit or disrupts cell cycle regulation and cell proliferation. Thus, the present invention provides compositions for treating or preventing cancer, which compositions include agents screened by any of the screening methods of the present invention, antisense nucleic acids and siRNAs of the STYK1 gene, or antibodies against the STYK1 polypeptide. The present compositions can be used for treating or preventing cancer, in particular, prostate cancer such as HRPC.

The compositions may be used as pharmaceuticals for humans and other mammals, such as mice, rats, guinea-pigs, rabbits, cats, dogs, sheep, pigs, cattle, monkeys, baboons, and chimpanzees.

In the context of the present invention, suitable pharmaceutical formulations for the active ingredients of the present invention detailed below (including screened agents, antisense nucleic acids, siRNA, antibodies, etc.) include those suitable for oral, rectal, nasal, topical (including buccal and sub-lingual), vaginal or parenteral (including intramuscular, subcutaneous and intravenous) administration, or for administration by inhalation or insufflation. Preferably, administration is intravenous. The formulations are optionally packaged in discrete dosage units.

Pharmaceutical formulations suitable for oral administration include capsules, microcapsules, cachets and tablets, each containing a predetermined amount of active ingredient. Suitable formulations also include powders, elixirs, granules, solutions, suspensions and emulsions. The active ingredient is optionally administered as a bolus electuary or paste. Alternatively, according to needs, the pharmaceutical composition may be administered non-orally, in the form of injections of sterile solutions or suspensions with water or any other pharmaceutically acceptable liquid. For example, the active ingredients of the present invention can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredient contained in such a preparation makes a suitable dosage within the indicated range acquirable.

Examples of additives that can be admixed into tablets and capsules include, but are not limited to, binders, such as gelatin, corn starch, tragacanth gum and arabic gum; excipients, such as crystalline cellulose; swelling agents, such as corn starch, gelatin and alginic acid; lubricants, such as magnesium stearate; sweeteners, such as sucrose, lactose or saccharin; and flavoring agents, such as peppermint, Gaultheria adenothrix oil and cherry. A tablet may be made by compression or molding, optionally with one or more formulational ingredients. Compressed tablets may be prepared by compressing in a suitable machine the active ingredients in a free-flowing form such as powder or granules, optionally mixed with a binder, lubricant, inert diluent, lubricating, surface active or dispersing agent. Molded tablets may be made via molding in a suitable machine a mixture of the powdered compound moistened with an inert liquid diluent. The tablets may be coated according to methods well known in the art. The tablets may optionally be formulated so as to provide slow or controlled release of the active ingredient in vivo. A package of tablets may contain one tablet to be taken on each of the month.

Furthermore, when the unit-dosage form is a capsule, a liquid carrier, such as oil, can be further included in addition to the above ingredients.

Oral fluid preparations may be in the form of, for example, aqueous or oily suspensions, solutions, emulsions, syrups or elixirs, or may be presented as a dry product for reconstitution with water or other suitable vehicle prior to use. Such liquid preparations may contain conventional additives such as suspending agents, emulsifying agents, non-aqueous vehicles (which may include edible oils) or preservatives.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Moreover, sterile composites for injection can be formulated following normal drug implementations using vehicles, such as distilled water, suitable for injection. Physiological saline, glucose, and other isotonic liquids, including adjuvants, such as D-sorbitol, D-mannose, D-mannitol, and sodium chloride, can be used as aqueous solutions for injection. These can be used in conjunction with suitable solubilizers, such as alcohol, for example, ethanol; polyalcohols, such as propylene glycol and polyethylene glycol; and non-ionic surfactants, such as Polysorbate 80 (TM) and HCO-50.

Sesame oil or soy-bean oil can be used as an oleaginous liquid, which may be used in conjunction with benzyl benzoate or benzyl alcohol as a solubilizer, and may be formulated with a buffer, such as phosphate buffer and sodium acetate buffer; a pain-killer, such as procaine hydrochloride; a stabilizer, such as benzyl alcohol and phenol; and/or an anti-oxidant. A prepared injection may be filled into a suitable ampoule.

Formulations for rectal administration include suppositories with standard carriers such as cocoa butter or polyethylene glycol. Formulations for topical administration in the mouth, for example, buccally or sublingually, include lozenges, which contain the active ingredient in a flavored base such as sucrose and acacia or tragacanth, and pastilles comprising the active ingredient in a base such as gelatin, glycerin, sucrose or acacia. For intra-nasal administration of an active ingredient, a liquid spray or dispersible powder or in the form of drops may be used. Drops may be formulated with an aqueous or non-aqueous base also comprising one or more dispersing agents, solubilizing agents or suspending agents.

For administration by inhalation the compositions are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compositions may take the form of a dry powder composition, for example, a powder mix of an active ingredient and a suitable powder base such as lactose or starch. The powder composition may be presented in unit dosage form in, for example, capsules, cartridges, gelatin or blister packs from which the powder may be administered with the aid of an inhalator or insufflators.

Other formulations include implantable devices and adhesive patches; which release a therapeutic agent.

When desired, the above-described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited under the item of 'V. Method for treating or preventing cancer' (infra), of each of the active ingredients of the present invention or an appropriate fraction thereof.

IV 1. Pharmaceutical Compositions Containing Screened Agents

The present invention provides compositions for treating or preventing cancers comprising any of the agents selected by the above-described screening methods of the present invention.

An agent screened by the method of the present invention can be directly administered or can be formulated into a dosage form according to any conventional pharmaceutical preparation method detailed above.

IV-2. Pharmaceutical Compositions Comprising siRNA

An siRNA against the STYK1 gene (hereinafter, also referred to as 'STYK1 siRNA') can be used to reduce the expression level of the gene. Herein, the term "siRNA" refers to a double-stranded RNA molecule which prevents translation of a target mRNA. In the context of the present invention, the siRNA comprises a sense nucleic acid sequence and an anti-sense nucleic acid sequence against the up-regulated marker gene, STYK1. The siRNA is constructed so that it both comprises a portion of the sense and complementary antisense sequences of the target gene (i.e., STYK1 gene), and may also be a single construct taking a hairpin structure, wherein the sense and antisense strands are linked via a single-strand. The siRNA may either be a dsRNA or shRNA.

An siRNA of the STYK1 gene hybridizes to target mRNA, i.e., associates with the normally single-stranded mRNA transcript and thereby interfering with translation of the mRNA, which finally decreases or inhibits production (expression) of the polypeptide encoded by the gene. Thus, an siRNA molecule of the invention can be defined by its ability to specifically hybridize to the mRNA of the STYK1 gene under stringent conditions. Herein, the portion of the siRNA that hybridizes with the target mRNA is referred to as "target sequence" or "target nucleic acid" or "target nucleotide".

In the context of the present invention, the target sequence of an siRNA is preferably less than 500, 200, 100, 50, or 25 base pairs in length. More preferably, the target sequencesequence of an siRNA is 19-25 base pairs in length. Exemplary target nucleic acid sequences of STYK1 siRNA includes the nucleotide sequences of SEQ ID NO: 5 or 6. The nucleotide "t" in the sequence should be replaced with "u" in RNA or derivatives thereof. Accordingly, for example, the present pharmaceutical composition may comprise a double-stranded RNA molecule (siRNA) comprising the nucleotide sequence 5'-GGTGGTACCTGAACTGTAT-3' (SEQ ID NO: 5) or 5'-GGTGGAGGAGTCATTTCAT-3' (SEQ ID NO: 6) as the sense strand. In order to enhance the inhibition activity of the siRNA, nucleotide "u" can be added to the 3'end of the target sequence in the antisense strand. The number of "u"s to be added is at least 2, generally 2 to 10, preferably 2 to 5. The added "u"s form a single strand at the 3' end of the antisense strand of the siRNA.

A loop sequence consisting of an arbitrary nucleotide sequence can be located between the sense and antisense strands in order to form a hairpin loop structure. Thus, the siRNA contained in the inventive composition may take the general formula 5'-[A]-[B]-[A']-3', wherein [A] is a polynucleotide strand which comprises the sense strand sequence of a target sequence specifically hybridizing to an mRNA or a cDNA of the STYK1 gene. Herein, the polynucleotide strand which comprises the sense strand sequence of a target sequence specifically hybridizing to an mRNA or a cDNA of the STYK1 gene may be referred to as "sense strand". In preferred embodiments, [A] is the sense strand; [B] is a single stranded polynucleotide consisting of 3 to 23 nucleotides; and [A'] is a polynucleotide strand which comprises the antisense strand sequence of a target sequence specifically hybridizing to an mRNA or a cDNA of the STYK1 gene (i.e., a sequence hybridizing to the target sequence of the sense strand [A]). Herein, the polynucleotide strand which comprises the antisense strand sequence of a target sequence specifically hybridizing to an mRNA or a cDNA of the STYK1 gene may be referred to as "antisense strand". The region [A] hybridizes to [A'], and then a loop consisting of the region [B] is formed. The loop sequence may be preferably 3 to 23 nucleotide in length. The loop sequence, for example, can be selected from a group consisting of following sequences (www.ambion.com/techlib/tb/tb_506.html):

CCC, CCACC, or CCACACC: Jacque J M et al., *Nature* 2002, 418: 435-8.

UUCG: Lee N S et al., *Nature Biotechnology* 2002, 20:500-5; Fruscoloni P et al., Proc Natl Acad Sci USA 2003, 100(4):1639-44.

UUCAAGAGA: Dykxhoorn D M et al., Nature Reviews Molecular Cell Biology 2003, 4:457-67.

'UUCAAGAGA ("ttcaagaga" in DNA)' is a particularly suitable loop sequence. Furthermore, loop sequence consisting of 23 nucleotides also provides an active siRNA (Jacque J M et al., Nature 2002, 418:435-8).

Exemplary hairpin siRNA suitable for use in the context of the present invention include, for STYK1-siRNA,

```
                                 (target sequence of SEQ ID NO: 5)
5'-GGUGGUACCUGAACUGUAU-[b]-AUACAGUUCAGGUACCACC-3';
and
                                 (target sequence of SEQ ID NO: 6)
5'-GGUGGAGGAGUCAUUUCAU-[b]-AUGAAAUGACUCCUCCACC-3'.
```

Other nucleotide sequences of suitable siRNAs for the present invention can be designed using an siRNA design computer program available from the Ambion web site (www.ambion.com/techlib/misc/siRNA_finder.html). The computer program selects nucleotide sequences for siRNA synthesis based on the following protocol.

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl et al. *Genes Cev* 1999, 13(24):3191-7 don't recommend against designing siRNA to the 5' and 3' untranslated regions (UTRs) and regions near the start codon (within 75 nucleotides) as these may be richer in regulatory protein binding sites. UTR-binding proteins and/or translation initiation complexes may interfere with binding of the siRNA endonuclease complex.
2. Compare the potential target sites to the human genome database and eliminate from consideration any target sequences with significant homology to other coding sequences. The homology search can be performed using BLAST (Altschul S F et al., *Nucleic Acids Res* 1997, 25:3389-402; *J Mol Biol* 1990, 215:403-10.), which can be found on the NCBI server at: www.ncbi.nlm.nih.gov/BLAST/.
3. Select qualifying target sequences for synthesis. At Ambion, preferably several target sequences can be selected along the length of the gene to evaluate.

Standard techniques are known in the art for introducing siRNA into cells. For example, an siRNA can be directly introduced into the cells in a form that is capable of binding to the mRNA transcripts. In these embodiments, the siRNA molecules are typically modified as described above for antisense molecules. Other modifications are also available, for example, cholesterol-conjugated siRNAs have shown improved pharmacological properties (Song et al., *Nature Med* 2003, 9:347-51). These conventionally used techniques may also be applied for the siRNAs contained in the present compositions.

Alternatively, a DNA encoding the siRNA may be carried in a vector (hereinafter, also referred to as 'siRNA vector') and the siRNA may be contained in the present composition in the form of vector which enables expression of the siRNA in vivo. Such vectors may be produced, for example, by cloning a portion of the target STYK1 gene sequence sufficient to inhibit the in vivo expression of the STYK1 gene into an expression vector having operatively-linked regulatory sequences (e.g., a RNA polymerase III transcription unit from the small nuclear RNA (snRNA) U6 or the human H1 RNA promoter) flanking the sequence in a manner that allows for expression (by transcription of the DNA molecule) of both strands (Lee N S et al., *Nature Biotechnology* 2002, 20: 500-5). For example, an RNA molecule that is antisense to mRNA of the STYK1 gene is transcribed by a first promoter (e.g., a promoter sequence 3' of the cloned DNA) and an RNA molecule that is the sense strand for the mRNA of the STYK1 gene is transcribed by a second promoter (e.g., a promoter sequence 5' of the cloned DNA). The sense and antisense strands hybridize in vivo to generate an siRNA construct for silencing the expression of the STYK1 gene. Alternatively, the sense and antisense strands may be transcribed together with the help of one promoter. In this case, the sense and antisense strands may be linked via a polynucleotide sequence to form a single-stranded siRNA construct having secondary structure, e.g., hairpin.

Thus, the present pharmaceutical composition for treating or preventing cancer comprises either the siRNA or a vector expressing the siRNA in vivo.

For introducing the siRNA vector into the cell, transfection-enhancing agent can be used. FuGENE6 (Roche diagnostics), Lipofectamine 2000 (Invitrogen), Oligofectamine (Invitrogen), and Nucleofector (Wako pure Chemical) are useful as the transfection-enhancing agent. Therefore, the present pharmaceutical composition may further include such transfection-enhancing agents.

IV-3. Pharmaceutical Compositions Comprising Antisense Nucleic Acids

Antisense nucleic acids targeting the STYK1 gene can be used to reduce the expression level of the gene, which is up-regulated in cancerous cells including prostate cancer cells (e.g., HRPC cells). Such antisense nucleic acids are useful for the treatment of cancer, in particular prostate cancer and thus are also encompassed by the present invention. An antisense nucleic acid acts by binding to the nucleotide sequence of the STYK1 gene, or mRNAs corresponding thereto, thereby inhibiting the transcription or translation of the gene, promoting the degradation of the mRNAs, and/or inhibiting the expression of the protein encoded by the gene.

Thus, as a result, an antisense nucleic acid inhibits the STYK1 protein to function in the cancerous cell. Herein, the phrase "antisense nucleic acids" refers to nucleotides that specifically hybridize to a target sequence and includes not only nucleotides that are entirely complementary to the target sequence but also that comprise mismatches of one or more nucleotides. For example, the antisense nucleic acids of the present invention include polynucleotides that have a homology of at least 70% or higher, preferably of at least 80% or higher, more preferably of at least 90% or higher, even more preferably of at least 95% or higher over a span of at least 15 continuous nucleotides of the STYK1 gene or the complementary sequence thereof. Algorithms known in the art can be used to determine such homology.

Antisense nucleic acids of the present invention act on cells producing proteins encoded by the STYK1 gene by binding to the DNA or mRNA of the gene, inhibiting their transcription or translation, promoting the degradation of the mRNA, and inhibiting the expression of the protein, finally inhibiting the protein to function.

Antisense nucleic acids of the present invention can be made into an external preparation, such as a liniment or a poultice, by admixing it with a suitable base material which is inactive against the nucleic acids.

Also, as needed, the antisense nucleic acids of the present invention can be formulated into tablets, powders, granules, capsules, liposome capsules, injections, solutions, nose-drops and freeze-drying agents by adding excipients, isotonic agents, solubilizers, stabilizers, preservatives, pain-killers, and such. An antisense-mounting medium can also be used to increase durability and membrane-permeability. Examples include, but are not limited to, liposomes, poly-L-lysine, lipids, cholesterol, lipofectin, or derivatives of these. These can be prepared by following known methods.

The antisense nucleic acids of the present invention inhibit the expression of the STYK1 protein and are useful for suppressing the biological activity of the protein. In addition, expression-inhibitors, comprising antisense nucleic acids of the present invention, are useful in that they can inhibit the biological activity of the STYK1 protein.

The antisense nucleic acids of present invention also include modified oligonucleotides. For example, thioated oligonucleotides may be used to confer nuclease resistance to an oligonucleotide.

IV-4. Pharmaceutical Compositions Comprising Antibodies

The function of a gene product of the STYK1 gene which is over-expressed in cancers, in particular prostate cancer (e.g., HRPC) can be inhibited by administering a compound that binds to or otherwise inhibits the function of the gene products. An antibody against the STYK1 polypeptide can be mentioned as such a compound and can be used as the active ingredient of a pharmaceutical composition for treating or preventing cancer.

The present invention relates to the use of antibodies against a protein encoded by the STYK1 gene, or fragments of the antibodies. As used herein, the term "antibody" refers to an immunoglobulin molecule having a specific structure, that interacts (i.e., binds) only with the antigen that was used for synthesizing the antibody (i.e., the gene product of an up-regulated marker) or with an antigen closely related thereto. Molecules comprising the antigen that was used for synthesizing the antibody and molecules comprising the epitope of the antigen recognized by the antibody can be mentioned as closely related antigens thereto.

Furthermore, an antibody used in the present pharmaceutical compositions may be a fragment of an antibody or a modified antibody, so long as it binds to the protein encoded by the STYK1 gene (e.g., an immunologically active fragment of anti-STYK1 antibody). For instance, the antibody fragment may be Fab, F(ab')$_2$, Fv, or single chain Fv (scFv), in which Fv fragments from H and L chains are ligated by an appropriate linker (Huston J S et al., *Proc Natl Acad Sci USA* 1988, 85:5879-83). Such antibody fragments may be generated by treating an antibody with an enzyme, such as papain or pepsin. Alternatively, a gene encoding the antibody fragment may be constructed, inserted into an expression vector, and expressed in an appropriate host cell (see, for example, Co M S et al., *J Immunol* 1994, 152:2968-76; Better M et al., *Methods Enzymol* 1989, 178:476-96; Pluckthun A et al., *Methods Enzymol* 1989, 178:497-515; Lamoyi E, *Methods Enzymol* 1986, 121:652-63; Rousseaux J et al., *Methods Enzymol* 1986, 121:663-9; Bird R E et al., *Trends Biotechnol* 1991, 9:132-7).

An antibody may be modified by conjugation with a variety of molecules, such as polyethylene glycol (PEG). The present invention includes such modified antibodies. The modified antibody can be obtained by chemically modifying an antibody. Such modification methods are conventional in the field.

Alternatively, the antibody used for the present invention may be a chimeric antibody having a variable region derived from a non-human antibody against the STYK1 polypeptide and a constant region derived from a human antibody, or a humanized antibody, comprising a complementarity determining region (CDR) derived from a non-human antibody, a frame work region (FR) and a constant region derived from a human antibody. Such antibodies can be prepared by using known technologies. Humanization can be performed by substituting rodent CDRs or CDR sequences for the corresponding sequences of a human antibody (see e.g., Verhoeyen et al., *Science* 1988, 239:1534-6). Accordingly, such humanized antibodies are chimeric antibodies, wherein substantially less than an intact human variable domain has been substituted by the corresponding sequence from a non-human species.

Complete human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom et al., *J Mol Biol* 1992, 227:381-8). Similarly, human antibodies can be made by introducing human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; and 5,661,016.

When the obtained antibody is to be administered to the human body (antibody treatment), a human antibody or a humanized antibody is preferable for reducing immunogenicity.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, saltingout, dialysis, SDS polyacrylamide gel electrophoresis, isoelectric focusing, and others (*Antibodies: A Laboratory Manual.* Ed Harlow and David Lane, Cold Spring Harbor Laboratory (1988)), but are not limited thereto. A protein A column and protein G column can be used as the affinity column. Exemplary protein A columns to be used include, for example, Hyper D, POROS, and Sepharose F. F. (Pharmacia).

Exemplary chromatography, with the exception of affinity includes, for example, ion-exchange chromatography, hydrophobic chromatography, gel filtration, reverse-phase chromatography, adsorption chromatography, and the like (*Strategies for Protein Purification and Characterization: A Laboratory Course Manual.* Ed Daniel R. Marshak et al., Cold Spring Harbor Laboratory Press (1996)). The chromatographic procedures can be carried out by liquid-phase chromatography, such as HPLC and FPLC.

V. Methods for Treating or Preventing Cancer:

Cancer therapies directed at specific molecular alterations that occur in cancer cells have been validated through clinical development and regulatory approval of anti-tumor pharmaceuticals such as trastuzumab (Herceptin) for the treatment of advanced cancers, imatinib mesylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F et al., *Clin Cancer Res* 2001, 7:2958-70, Review; Slamon D J et al., *N Engl J Med* 2001, 344:783-92; Rehwald U et al., *Blood* 2003, 101:420-4; Fang G et al., *Blood* 2000, 96:2246-53). These drugs are clinically effective and better tolerated than traditional anti-tumor agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L, *Oncology* 2002, 63 Suppl 1:47-56; Klejman A et al., *Oncogene* 2002, 21:5868-76). Therefore, future cancer treatments will probably involve combining conventional drugs with target-specific agents aimed at different characteristics of tumor cells such as angiogenesis and invasiveness.

These modulatory methods can be performed ex vivo or in vitro (e.g., by culturing the cell with the agent) or, alternatively, in vivo (e.g., by administering the agent to a subject). The methods involve administering a protein or combination of proteins or a nucleic acid molecule or combination of nucleic acid molecules as therapy to counteract aberrant expression of the differentially expressed genes or aberrant activity of their gene products.

Diseases and disorders that are characterized by increased (relative to a subject not suffering from the disease or disorder) expression levels or biological activities of genes and gene products, respectively, may be treated with therapeutics that antagonize (i.e., reduce or inhibit) activity of the over-expressed gene. Therapeutics that antagonize activity can be administered therapeutically or prophylactically.

Accordingly, therapeutics that may be utilized in the context of the present invention include, e.g., (i) a polypeptide of the over-expressed STYKJ gene or analogs, derivatives, fragments or homologs thereof; (ii) antibodies against the over-expressed gene or gene products; (iii) nucleic acids encoding the over-expressed gene; (iv) antisense nucleic acids or nucleic acids that are "dysfunctional" (i.e., due to a heterologous insertion within the nucleic acids of over-expressed gene); (v) small interfering RNA (siRNA); or (vi) modulators (i.e., inhibitors, antagonists that alter the interaction between an over-expressed polypeptide and its binding partner). The dysfunctional antisense molecules are utilized to "knockout" endogenous function of a polypeptide by homologous recombination (see, e.g., Capecchi, *Science* 1989, 244: 1288-92).

Increased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease, such that a disease or disorder is prevented or, alternatively, delayed in its progression.

Therapeutic methods of the present invention may include the step of contacting a cell with an agent that modulates one or more of the activities of the STYK1 gene products. Examples of agent that modulates protein activity include, but are not limited to, nucleic acids, proteins, naturally occurring cognate ligands of such proteins, peptides, peptidomimetics, and other small molecule.

Thus, the present invention provides methods for treating or alleviating a symptom of cancer, or preventing cancer in a subject by decreasing the expression of the STYK1 gene or the activity of the gene product. The present method is particularly suited for treating or preventing prostate cancer, such as HRPC.

Suitable therapeutics can be administered prophylactically or therapeutically to a subject suffering from or at risk of (or susceptible to) developing cancers. Such subjects can be identified by using standard clinical methods or by detecting an aberrant expression level ("up-regulation" or "over-expression") of the STYK1 gene or aberrant activity of the gene product.

According to an aspect of the present invention, an agent screened through the present method may be used for treating or preventing cancer. Methods well known to those skilled in the art may be used to administer the agents to patients, for example, as an intraarterial, intravenous, or percutaneous injection or as an intranasal, transbronchial, intramuscular, or oral administration. If said agent is encodable by a DNA, the DNA can be inserted into a vector for gene therapy and the vector administered to a patient to perform the therapy.

The dosage and methods for administration vary according to the body-weight, age, sex, symptom, condition of the patient to be treated and the administration method; however, one skilled in the art can routinely select suitable dosage and administration method.

For example, although the dose of an agent that binds to the STYK1 polypeptide and regulates the activity of the polypeptide depends on the aforementioned various factors, the dose is generally about 0.1 mg to about 100 mg per day, preferably about 1.0 mg to about 50 mg per day and more preferably about 1.0 mg to about 20 mg per day, when administered orally to a normal adult human (60 kg weight).

When administering the agent parenterally, in the form of an injection to a normal adult human (60 kg weight), although there are some differences according to the patient, target organ, symptoms and methods for administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount may be routinely calculated by converting to 60 kg of bodyweight.

Similarly, a pharmaceutical composition of the present invention may be used for treating or preventing cancer. Methods well known to those skilled in the art may be used to administer the compositions to patients, for example, as an intraarterial, intravenous, or percutaneous injection or as an intranasal, transbronchial, intramuscular, or oral administration.

For each of the aforementioned conditions, the compositions, e.g., polypeptides and organic compounds, can be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age, body weight and sex of the subject, the precise disorder being treated, and its severity. Also the route of administration may vary depending upon the condition and its severity. In any event, appropriate and optimum dosages may be routinely calculated by those skilled in the art, taking into consideration the above-mentioned factors.

In particular, an antisense nucleic acids against the STYK1 gene can be given to the patient by direct application onto the ailing site or by injection into a blood vessel so that it will reach the site of ailment.

The dosage of the antisense nucleic acid derivatives of the present invention can be adjusted suitably according to the patient's condition and used in desired amounts. For example, a dose range of 0.1 to 100 mg/kg, preferably 0.1 to 50 mg/kg can be administered.

VI. Vaccinating Against Cancer:

The present invention relates to a method for treating or preventing cancers, in particular, prostate cancer (e.g., HRPC) in a subject comprising the step of administering to said subject a vaccine comprising a polypeptide encoded by the STYK1 gene, an immunologically active fragment of said polypeptide, or a polynucleotide encoding such a polypeptide or fragment thereof. In the present invention, vaccines against cancers refer to substances that have the ability to induce anti-tumor immunity upon inoculation into animals. Administration of such a vaccine induces anti-tumor immunity in the subject. Thus, the present invention also relates to a method for inducing anti-tumor immunity in a subject in need thereof by administering to said subject a vaccine comprising a polypeptide encoded by the STYK1 gene, an immunologically active fragment of said polypeptide, or a polynucleotide encoding such a polypeptide or fragment thereof These methods are particularly suited for treating or preventing prostate cancer, and more preferably HRPC.

In some cases, the STYK1 protein or immunologically active fragments thereof may be administered in a form bound to T cell receptors (TCRs) or presented by APCs, such as macrophage, dendritic cell (DC), B-cells, or PBMCs. Due to the strong antigen presenting ability of DC, the use of DC is most preferable among the APCs.

In general, anti-tumor immunity includes immune responses such as follows:
  induction of cytotoxic lymphocytes against tumors,
  induction of antibodies that recognize tumors, and
  induction of anti-tumor cytokine production.

Therefore, when a certain protein induces any one of these immune responses upon inoculation into an animal, the protein is determined to have anti-tumor immunity inducing effect. Any protein fragment of the STYK1 polypeptide may be used as an immunologically active fragment of the present methods.

The induction of the anti-tumor immunity by a protein can be detected by observing in vivo or in vitro the response of the immune system in the host against the protein.

For example, a method for detecting the induction of CTLs is well known. Specifically, a foreign substance that enters the living body is presented to T cells and B cells by the action of APCs. T cells that respond to the antigen presented by the APCs in an antigen specific manner differentiate into CTLs due to stimulation by the antigen, and then proliferate (this is referred to as activation of T cells). Therefore, CTL induction by a certain peptide can be evaluated by presenting the peptide to a T cell via an APC, and detecting the induction of CTLs. Furthermore, APCs have the effect of activating CD4+ T cells, CD8+ T cells, macrophages, eosinophils, and NK cells. Since CD4+ T cells and CD8+ T cells are also important in anti-tumor immunity, the anti-tumor immunity-inducing action of the peptide can be evaluated using the activation effect of these cells as indicators.

A method for evaluating the inducing action of CTLs using DCs as the APC is well known in the art. DCs are representative APCs having the strongest CTL-inducing action among APCs. To determine whether a fragment of the STYK1 polypeptide is immunological active and can be used in the present method, a test polypeptide (i.e., any fragment of the STYK1 polypeptide) is initially contacted with DCs, and then the DCs are contacted with T cells. Detection of T cells having cytotoxic effects against the cells of interest after the contact with DC shows that the test polypeptide has an activity of inducing the cytotoxic T cells. Activity of CTLs against tumors can be detected, for example, using the lysis of $^{51}$Cr-labeled tumor cells as the indicator. Alternatively, the methods for evaluating the degree of tumor cell damage using $^{3}$H-thymidine uptake activity or LDH (lactose dehydrogenase)-release as the indicator is also well known.

Apart from DCs, PBMCs may also be used as the APC. The induction of CTLs has been reported to be enhanced by culturing PBMCs in the presence of GM-CSF and IL-4. Similarly, CTLs have been shown to be induced by culturing PBMCs in the presence of keyhole limpet hemocyanin (KLH) and IL-7.

Test polypeptides confirmed to possess CTL-inducing activity by these methods are deemed to be polypeptides having DC activation effect and subsequent CTL-inducing activity. Therefore, polypeptides that induce CTLs against tumor cells are useful as vaccines against tumors. Furthermore, APCs that have acquired the ability to induce CTLs against tumors through contact with the polypeptides are also useful as vaccines against tumors. Furthermore, CTLs that have acquired cytotoxicity due to presentation of the polypeptide antigens by APCs can be also used as vaccines against tumors. Such therapeutic methods for tumors, using anti-tumor immunity due to APCs and CTLs, are referred to as cellular immunotherapy.

Generally, when using a polypeptide for cellular immunotherapy, efficiency of the CTL-induction is known to be increased by combining a plurality of polypeptides having different structures and contacting them with DCs. Therefore, when stimulating DCs with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by these antibodies, the polypeptide is deemed to have the ability to induce anti-tumor immunity.

Anti-tumor immunity is induced by administering the vaccines of this invention, and the induction of anti-tumor immunity enables treatment and prevention of cancers. Therapy against cancer or prevention of the onset of cancer includes any of the following steps, such as inhibition of the growth of cancer cells, involution of cancer, and suppression of the occurrence of cancer. A decrease in mortality and morbidity of individuals having cancer, decrease in the levels of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analysis.

The above-mentioned STYK1 polypeptide or fragments thereof having immunological activity or a vector encoding them may be combined with an adjuvant. An adjuvant refers to a compound that enhances the immune response against the STYK1 polypeptide when administered together (or successively) with the polypeptide or fragment having immunological activity. Exemplary adjuvants include, but are not limited to, cholera toxin, salmonella toxin, alum, and such, but are not limited thereto. Furthermore, the vaccines of this invention may be combined appropriately with a pharmaceutically acceptable carrier. Examples of such carriers include sterilized water, physiological saline, phosphate buffer, culture fluid, and such. Furthermore, the vaccine may contain as necessary, stabilizers, suspensions, preservatives, surfactants, and such. The vaccine can be administered systemically or locally. Vaccine administration can be performed by single administration, or boosted by multiple administrations.

When using APCs or CTLs as the vaccines of this invention, tumors can be treated or prevented, for example, by the ex vivo method. More specifically, PBMCs of the subject receiving treatment or prevention are collected, the cells are contacted with the STYK1 polypeptide or fragments thereof ex vivo, and following the induction of APCs or CTLs, the cells may be administered to the subject. APCs can be also induced by introducing a vector encoding the polypeptide into PBMCs ex vivo. APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells are derived, but also against similar types of tumors from other individuals.

Furthermore, pharmaceutical compositions for treating or preventing cell proliferative diseases, such as cancers, comprising a pharmaceutically effective amount of the STYK1 polypeptide or immunological active fragments thereof is provided. Such pharmaceutical compositions may be used for raising anti tumor immunity.

VII. Double-stranded Molecules and Vectors Encoding Them

According to the present invention, siRNA comprising either of the sequences of SEQ ID NOs: 5 and 6 was demonstrated to suppress cell growth or viability of cells expressing the STYK1 gene. Therefore, double-stranded molecules comprising any of these sequences and vectors expressing the molecules are considered to serve as preferable pharmaceutics for treating or preventing diseases which involve the proliferation of STYK1 gene expressing cells (e.g., prostate cancer such as HRPC). Thus, according to an aspect, the present invention provides double-stranded molecules comprising a sequence selected from the group of SEQ ID NOs: 5 and 6, and vectors expressing the molecules. More specifically, the present invention provides a double-stranded molecule, when introduced into a cell expressing the STYK1 gene, inhibits expression of the gene, which molecule comprises a sense strand and an antisense strand, wherein the sense strand comprises a nucleotide sequence selected from the group consisting of SEQ ID NOs: 5 and 6 as the target sequence, and the antisense strand comprises a nucleotide sequence complementary to the target sequence of the sense strand so that the sense and antisense strands hybridize to each other to form the double-stranded molecule.

The target sequence comprised in the sense strand may consist of a sequence of a portion of SEQ ID NO: 8 that is less than about 500, 400, 300, 200, 100, 75, 50 or 25 contiguous nucleotides. For example, the target sequence may be from about 19 to about 25 contiguous nucleotides from the nucleotide sequence of SEQ ID NO: 8. The present invention is not limited thereto, but suitable target sequences include the sequences of SEQ ID NOs: 5 and 6.

The double-stranded molecule of the present invention may be composed of two polynucleotide constructs, i.e., a polynucleotide comprising the sense strand and a polynucleotide comprising the antisense strand. Alternatively, the molecule may be composed of one polynucleotide construct; i.e., a polynucleotide comprising both the sense strand and the antisense strand, wherein the sense and antisense strands are linked via a single-stranded polynucleotide which enables hybridization of the target sequences within the sense and antisense strands by forming a hairpin structure. Herein, the single-stranded polynucleotide may also be referred to as "loop sequence" or "single-strand". The single-stranded polynucleotide linking the sense and antisense strands may consist of 3 to 23 nucleotides. See under the item of "IV-2. Pharmaceutical compositions comprising siRNA" for more details on the double-stranded molecule of the present invention.

The double-stranded molecules of the invention may contain one or more modified nucleotides and/or non-phosphodiester linkages. Chemical modifications well known in the art are capable of increasing stability, availability, and/or cell uptake of the double-stranded molecule. The skilled person will be aware of other types of chemical modification which may be incorporated into the present molecules (WO03/070744; WO2005/045037). In one embodiment, modifications can be used to provide improved resistance to degradation or improved uptake. Examples of such modifications include phosphorothioate linkages, 2'-O-methyl ribonucleotides (especially on the sense strand of a double-stranded molecule), 2'-deoxy-fluoro ribonucleotides, 2'-deoxy ribonucleotides, "universal base" nucleotides, 5'-C-methyl nucleotides, and inverted deoxyabasic residue incorporation (US20060122137).

In another embodiment, modifications can be used to enhance the stability or to increase targeting efficiency of the double-stranded molecule. Modifications include chemical cross linking between the two complementary strands of a double-stranded molecule, chemical modification of a 3' or 5' terminus of a strand of a double-stranded molecule, sugar modifications, nucleobase modifications and/or backbone modifications, 2-fluoro modified ribonucleotides and 2'-deoxy ribonucleotides (WO2004/029212). In another embodiment, modifications can be used to increased or decreased affinity for the complementary nucleotides in the target mRNA and/or in the complementary double-stranded molecule strand (WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyi, or 7-alkenyi purine. In another embodiment, when the double-stranded molecule is a double-stranded molecule with a 3' overhang, the 3'-terminal nucleotide overhanging nucleotides may be replaced by deoxyribonucleotides (Elbashir S M et al., *Genes Dev* 2001 Jan. 15, 15(2): 188-200). For further details, published documents such as US20060234970 are available. The present invention is not limited to these examples and any known chemical modifications may be employed for the double-stranded molecules of the present invention so long as the resulting molecule retains the ability to inhibit the expression of the target gene.

Furthermore, the double-stranded molecules of the invention may comprise both DNA and RNA, e.g., dsD/R-NA or shD/R-NA. Specifically, a hybrid polynucleotide of a DNA strand and an RNA strand or a DNA-RNA chimera polynucleotide shows increased stability. Mixing of DNA and RNA, i.e., a hybrid type double-stranded molecule consisting of a DNA strand (polynucleotide) and an RNA strand (polynucleotide), a chimera type double-stranded molecule comprising both DNA and RNA on any or both of the single strands (polynucleotides), or the like may be formed for enhancing stability of the double-stranded molecule. The hybrid of a DNA strand and an RNA strand may be the hybrid in which either the sense strand is DNA and the antisense strand is RNA, or the opposite so long as it has an activity to inhibit expression of the target gene when introduced into a cell expressing the gene. Preferably, the sense strand polynucleotide is DNA and the antisense strand polynucleotide is RNA. Also, the chimera type double-stranded molecule may be either where both of the sense and antisense strands are composed of DNA and RNA, or where any one of the sense and antisense strands is composed of DNA and RNA so long as it has an activity to inhibit expression of the target gene when introduced into a cell expressing the gene.

In order to enhance stability of the double-stranded molecule, the molecule preferably contains as much DNA as possible, whereas to induce inhibition of the target gene expression, the molecule is required to be RNA within a range to induce sufficient inhibition of the expression. As a preferred example of the chimera type double-stranded molecule, an upstream partial region (i.e., a region flanking to the target sequence or complementary sequence thereof within the sense or antisense strands) of the double-stranded molecule is RNA. Preferably, the upstream partial region indicates the 5' side (5'-end) of the sense strand and the 3' side (3'-end) of the antisense strand. That is, in preferable embodiments, a region flanking to the 3'-end of the antisense strand, or both of a region flanking to the 5'-end of sense strand and a region flanking to the 3-end of antisense strand consists of RNA. For instance, the chimera or hybrid type double-stranded molecule of the present invention comprise following combinations.

sense strand: 5'-[DNA]-3'
        3'-(RNA)-[DNA]-5': antisense strand,
    sense strand: 5'-(RNA)-[DNA]-3'
        3'-(RNA)-[DNA]-5': antisense strand, and
    sense strand: 5'-(RNA)-[DNA]-3'
        3'-(RNA)-5': antisense strand.

The upstream partial region preferably is a domain consisting of 9 to 13 nucleotides counted from the terminus of the target sequence or complementary sequence thereto within the sense or antisense strands of the double-stranded molecules. Moreover, preferred examples of such chimera type double-stranded molecules include those having a strand length of 19 to 21 nucleotides in which at least the upstream half region (5' side region for the sense strand and 3' side region for the antisense strand) of the polynucleotide is RNA and the other half is DNA. In such a chimera type double-stranded molecule, the effect to inhibit expression of the target gene is much higher when the entire antisense strand is RNA (US20050004064).

In the present invention, the double-stranded molecule may form a hairpin, such as a short hairpin RNA (shRNA) and short hairpin consisting of DNA and RNA (shD/R-NA). The shRNA or shD/R-NA is a sequence of RNA or mixture of RNA and DNA making a tight hairpin turn that can be used to silence gene expression via RNA interference. The shRNA or shD/R-NA comprises the sense target sequence and the antisense target sequence on a single strand wherein the sequences are separated by a loop sequence. Generally, the hairpin structure is cleaved by the cellular machinery into dsRNA or dsD/R-NA, which is then bound to the RNA-induced silencing complex (RISC). This complex binds to and cleaves mRNAs which match the target sequence of the dsRNA or dsD/R-NA.

Hereinafter, the present invention is described in more detail with reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

I. Materials and Methods

1. Cell Lines and Tissue Specimens

Human PC cell lines LNCaP, 22Rv1, PC-3, and DU145 were obtained from the American Type Culture Collection (ATCC, Rockville, Md.). C4-2B, hormone-refractory derivative from LNCaP, was obtained from ViroMed Laboratories (Minnetonka, Minn.). All of them were cultured as monolayers in appropriate medium supplemented with 10% fetal bovine serum. Cells were maintained at 37° C. in an atmosphere of humidified air with 5% $CO_2$.

2. Semi-quantitative RT-PCR

Microdissection of HRPC cells and normal prostate epithelium were described previously (Ashida S, et al. *Cancer Res* 2004, 64: 5963-72). RNA from the HRPC cells and normal pancreatic ductal cells were subjected to two-round T7-based RNA amplification (Epicentre Technologies, Madison, Wis.) and subsequent synthesis of single-strand cDNA. Total RNAs from human prostate cancer cell lines were extracted using TRIzol reagent (Invitrogen, Carlsbad, Calif.) according to the manufacturer's recommendation. Extracted RNAs were treated with DNase I (Roche, Mannheim, Germany) and reverse-transcribed to single-stranded cDNAs using oligo (dT) primer with Superscript II reverse transcriptase (Invitrogen). The primer sequences employed by the present inventors were:

```
5'-TTGGCTTGACTCAGGATTTA-3'      (SEQ ID NO: 1)
and

5'-ATGCTATCACCTCCCCTGTG-3';     (SEQ ID NO: 2)
for β-actin (ACTB)
and

5'-GGACATGGATTCTTGATCTTCCT-3'   (SEQ ID NO: 3)
and

5'-ATGTGGTTCCAGAGGAAACTAGC-3'   (SEQ ID NO: 4)
for STYK1.
```

The RT-PCR exponential phase was determined to allow semi-quantitative comparisons among cDNAs developed from identical reactions. Each PCR regime involved a 95° C., 5-min initial denaturation step followed by 20 cycles (for ACTB) or 30 cycles (for STYK1) at 95° C. for 30 s, 55° C. for 30 s, and 72° C. for 30 s, on a Gene Amp PCR system 9600 (PE Applied Biosystems, Foster, Calif.).

3. Northern Blot Analysis

Present inventors extracted total RNAs from several PC cell lines using TRIzol reagent (Invitrogen, Carlsbad, Calif.) and performed Northern blot analysis. After treatment with DNase I (Nippon Gene, Osaka, Japan), mRNA was purified with Micro-FastTrack (Invitrogen), according to the manufacturer's protocols. A 1-μg aliquot of each mRNA from PC cell lines, as well as those isolated from normal human adult heart, lung, liver, kidney, brain, and prostate (BD Biosciences, Palo Alto, Calif.), were separated on 1% denaturing agarose gels and transferred onto nylon membranes. The 247-bp probe specific to STYK1 was prepared by PCR using the primers described above. Hybridization with a random-primed, $\alpha^{32}$P-dCTP-labeled probe was carried out according to the instructions for MegaPrime DNA labeling system (Amersham Biosciences, Buckinghamshire, UK). Prehybridization, hybridization and washing were performed according to the supplier's recommendations. The blots were auto-radiographed with intensifying screens at −80° C. for 7 days.

4. Small Interfering RNA (siRNA)-expressing Constructs and Transfection

To knock down endogenous STYK1 expression in PC cells, present inventors used psiU6BX3.0 vector for the expression of short hairpin RNA against a target gene as described previously (Anazawa Y, et al. Cancer Res 2003, 65: 4578-86). The target sequences of the synthetic oligonucleotides for siRNA for STYK1 were as follows:

si1: 5'-GGTGGTACCTGAACTGTAT-3' (SEQ ID NO: 5);
si3: 5'-GGTGGAGGAGTCATTTCAT-3' (SEQ ID NO: 6); and
scramble-si: 5'-GCGCGCTTTGTAGGATTCG-3' (SEQ ID NO: 7) (as negative control). PC cell lines, 22Rv1 and LNCaP, which expresses STYK1, were plated onto 6-well plates, and transfected with plasmid designed to express siRNA to STYK1 (8 μg) using FuGENE6 (Roche) according to manufacture's instruction. Cells were selected with 0.4 mg/ml (for 22Rv1) or 0.8 mg/ml (for LNCaP) of Geneticin (Sigma-Aldrich) for 9 days, and then harvested to analyze the knockdown effect on STYK1 expression. For colony formation assay, transfectants expressing siRNAs were grown for 24 days in media containing Geneticin. After fixation with 4% paraformaldehyde, transfected cells were stained with Giemsa solution to assess colony formation. Cell viability was quantified using Cell counting kit-8 (DOJINDO, Kumamoto, Japan). After 24 days of culture in the Geneticin-containing medium, the solution was added to a final concentration of 10%. Following incubation at 37° C. for 2 hr, absorbance at 450nm was measured with MicroPlate Reader 550 (Bio-Rad, Hercules, Calif.).

5. Antibody Generation and Immunohistochemistry

The cDNA fragment encoding the partial-length STYK1 (codon 50 to 150) was generated using PrimeSTAR polymerase (TAKARA, Japan) using the primers 5'-agagaacaaa-gaactcaacagc-3' (SEQ ID NO:19) and 5'-tcataaagcct-tgagaataacac-3' (SEQ ID NO:20), and cloned into pGEX-6P-1 (GE Healthcare). The recombinant STYK1 protein fused with GST was expressed in E. coli, BL21 codon plus (Stratagene, La Jolla, Calif.), and purified with GST bead under native condition according to the supplier's protocol. The purified GST-fused STYK1 was cleaved by PreScission Protease (GE Healthcare) on the bead, and the recombinant STYK1 protein was purified. This purified recombinant STYK1 protein was immunized into rabbits, and the immune sera were purified on affinity-columns packed with Affi-Gel 10 activated affinity media (Bio-Rad Laboratories, Hercules, Calif.) conjugating recombinant STYK1 protein with accordance of basic methodology.

Conventional sections from PC tissues were obtained from surgical specimens, and HRPC tissues were obtained by autopsy and TUR-P (Tamura et al. Cancer Res 67,5117-25, 2007). The sections were deparaffinized and autoclaved at 108° C. in Dako Cytomation Target Retrieval Solution High pH (Dako, Carpinteria, Calif.) for 15 min. After blocking of endogenous peroxidase and proteins, the sections were incubated with anti-STYK1 antibody (diluted by 1:10) at room temperature for 60 min. After washing with PBS, immunodetection was performed with peroxidase labeled anti-rabbit immunoglobulin (Envision kit, Dako). Finally, the reactants were developed with 3, 3'-diaminobenzidine (Dako). Counterstaining was performed using hematoxylin.

II. Results

1. STYK1 was Overexpressed in HRPC Cells

Among dozens of the up-regulated genes in HRPC cells identified through detailed expression profile analysis, the present inventors focused on the STYK1 gene (GeneBank Accession No. NM_018423 (SEQ ID NO: 8) coding for the amino acid sequence set forth in SEQ ID NO: 9) for further expressional and functional analysis. The semi-quantitative RT-PCR analysis using RNAs from microdissected HRPC cells and normal prostate epithelial cells demonstrated that expression of STYK1 was significantly up-regulated in HRPC cells compared with normal prostate epithelial cells (FIG. 1A). Further comparisons of STYK1 expression patterns in PC cells and normal tissues by Northern blot analysis apparently revealed strong and specific expression of STYK1 in PC cells although its expression was also observed in normal brain (FIG. 1B). Northern blot analysis on various human normal adult organs showed STYK1 expression in prostate (FIG. 1C).

2. Knockdown of STYK1 by siRNA on PC Cell Lines.

To investigate the potential growth-promoting role of STYK1 aberrant expression and potentiality of STYK1 as a molecular target, the present inventors constructed several siRNA-expression vectors to examine their knockdown effects on two STYK1-expressing PC cell lines, 22Rv1 and LNCaP. After transfection of each of these siRNA-expressing constructs into the cells, semi-quantitative RT-PCR was performed. The results showed that si1 and si3 constructs, but none of the other constructs, significantly knocked down endogenous STYK1 expression (FIGS. 2A and D). After 24-day selection in culture medium containing Geneticin, MTT assay (FIGS. 2B and E) and colony formation assay (FIGS. 2C and F) was performed to demonstrate that introduction of si1 and si3 in 22Rv1 and LNCaP cells drastically attenuated cell growth or viability of the cells, while other siRNAs, which did not affect STYK1 expression did not affect cell growth either.

3. Immunohistochemical Analysis

The polyclonal antibody specific to human STYK1 was generated, and to validate STYK1 protein expression in PC cells, the immunohistochemical analysis was performed with 22 clinical PC tissues (16 hormone-sensitive or naïve PCs and 6 HRPCs). As indicated by northern blot analysis and RT-PCR analysis, normal prostate epithelium in PC tissues showed week positivity of STYK1 (FIG. 3A), and 14/16 (88%) of hormone-sensitive or naïve PCs showed week positivity of STYK1 as well (FIG. 3B). On the other hand, all of six HRPCs and 2/16 (15%) of hormone-sensitive or naive PC showed strong positivity of STYK1 (FIG. 3C), which was consistent with the result from RT-PCR analysis.

III. Discussion on the Results

The emergence of HRPC is the most serious problem in the clinical setting of prostate cancer. No effective therapeutic options have been existed for prostate cancer that progress after androgen ablation therapy. Very recently, docetaxel based chemotherapy has been demonstrated to extend survival in 2 large randomized trials (Tannock I F, et al. *N Engl J Med* 2004, 351: 1502-12; Petrylak D P, et al. *N Engl J Med* 2004, 351: 1513-20). However, the therapy for HRPC is still a big challenge and novel molecular targeting therapies for HRPC are urgently required. In this invention, the present inventors identified overexpression of STYK1 which encodes a kinase, the most promising molecular target. According to the human Kinome Map (www.cellsignal.com/reference/kinase/kinome.html), STYK1 is mapped at the trunk of the tyrosine kinase branch (Manning C, et al. *Science* 2002, 298: 1912-34). Tyrosine phosphorylation is an important signaling mechanism in eukaryotic cells. In cancer, oncogenic activation of tyrosine kinases is a common feature, and novel anticancer drugs have been introduced which target these enzymes including, such as imatinib targeting Bcr-Abl, and c-kit and gefinitib targeting EGFR (Manning C, et al. *Science* 2002, 298: 1912-34; Sausville E A, et al. *Nature Rev Drug Dis* 2003, 313: 296-313). The identification of the substrate of STYK1 kinase and small molecules specifically inhibiting the kinase activity of the kinase are expected to provide novel therapeutic approach against HRPCs.

Industrial Applicability

The gene-expression analysis of cancers described herein using the combination of laser-capture dissection and genome-wide cDNA microarray has identified specific genes as targets for cancer prevention and therapy. Based on the expression of a differentially expressed gene, STYK1, the present invention provides a molecular diagnostic marker for identifying and detecting cancer, in particular, prostate cancer.

The data provided herein add to a comprehensive understanding of cancers, facilitate development of novel diagnostic strategies, and provide clues for identification of molecular targets for therapeutic drugs and preventative agents. Such information contributes to a more profound understanding of tumorigenesis, and provide indicators for developing novel strategies for diagnosis, treatment, and ultimately prevention of cancers.

All patents, patent applications, and publications cited herein are incorporated by reference in their entirety.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method for diagnosing prostate cancer in a subject, comprising the step of determining the expression level of the STYK1 gene in a subject-derived biological sample comprising prostate epithelial cell, wherein an increase in said expression level as compared to a normal control level of said gene in prostate epithelial cell obtained from non-cancerous tissue indicates that said subject suffers from prostate cancer.

2. The method of claim 1, wherein said expression level is at least 10% greater than the normal control level.

3. The method of claim 1, wherein said expression level is determined by any of the methods selected from the group consisting of:
    (a) detecting mRNA of the STYK1 gene;
    (b) detecting a protein encoded by the STYK1 gene; and
    (c) detecting a biological activity of the protein encoded by the STYK1 gene.

4. The method of claim 1, wherein said cancer is hormone refractory prostate cancer (HRPC).

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 1
ttggcttgac tcaggattta                                            20

<210> SEQ ID NO 2
<211> LENGTH: 20
<212> TYPE: DNA
<213> ORGANISM: Artificial
<220> FEATURE:
<223> OTHER INFORMATION: An artificially synthesized primer sequence for
      RT-PCR

<400> SEQUENCE: 2
atgctatcac ctcccctgtg                                            20

<210> SEQ ID NO 3
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 3
ggacatggat tcttgatctt cct                                        23

```
<210> SEQ ID NO 4
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 4
atgtggttcc agaggaaact agc                                            23

<210> SEQ ID NO 5
<211> LENGTH: 19
<212> TYPE: DNA
<213> ORGANISM: Artificial
<220> FEATURE:
<223> OTHER INFORMATION: A target sequence for siRNA

<400> SEQUENCE: 5
ggtggtacct gaactgtat                                                 19

<210> SEQ ID NO 6
<211> LENGTH: 19
<212> TYPE: DNA
<213> ORGANISM: Artificial
<220> FEATURE:
<223> OTHER INFORMATION: A target sequence for siRNA

<400> SEQUENCE: 6
ggtggaggag tcatttcat                                                 19

<210> SEQ ID NO 7
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 7
gcgcgctttg taggattcg                                                 19

<210> SEQ ID NO 8
<211> LENGTH: 2844
<212> TYPE: DNA
<213> ORGANISM: Homo sapiens
<220> FEATURE:
<221> NAME/KEY: CDS
<222> LOCATION: (270)..(1535)

<400> SEQUENCE: 8 acccaacccct gtcattattt cccctccgac tgggccggtg ccatcggaaa ccggagtgac    60
cagaggaggg acacgcatcc aatttcactg ggctgcaaga tatcaataag ccttgcctct   120
ttaaactact tatgtacaaa taaaagtgat ggtgagaacc tggctcagga aatgcagtag   180
caggccatat tgcatccaaa ggaattactc acagctgtgc tgtgtgcatt ctctgtgggc   240
ctagcaggga aggggacagc cctgtggca atg ggc atg aca cgg atg ctc ctg     293
                                 Met Gly Met Thr Arg Met Leu Leu
                                  1               5 gaa tgc agt ctc agt gac aag ttg tgt gtc atc cag gag aag cag tat     341
Glu Cys Ser Leu Ser Asp Lys Leu Cys Val Ile Gln Glu Lys Gln Tyr
         10                  15                  20 gaa gtg att atc gtc cca act ttg ttg gtt act atc ttc ctc atc ctt     389
Glu Val Ile Ile Val Pro Thr Leu Leu Val Thr Ile Phe Leu Ile Leu
 25                  30                  35                  40
```

| | | |
|---|---|---|
| ctt ggg gtc atc ctg tgg ctt ttt atc aga gaa caa aga act caa cag<br>Leu Gly Val Ile Leu Trp Leu Phe Ile Arg Glu Gln Arg Thr Gln Gln<br>                  45                            50                       55 | 437 |
| cag cgt tct gga cct caa ggc att gcc cct gtt cct cca cct agg gac<br>Gln Arg Ser Gly Pro Gln Gly Ile Ala Pro Val Pro Pro Pro Arg Asp<br>                60                            65                       70 | 485 |
| cta agc tgg gaa gca gga cat gga gga aat gtg gct ttg cca ctt aag<br>Leu Ser Trp Glu Ala Gly His Gly Gly Asn Val Ala Leu Pro Leu Lys<br>           75                            80                            85 | 533 |
| gag aca tcc gtg gaa aac ttt ctg gga gct acc aca cct gcc ctg gct<br>Glu Thr Ser Val Glu Asn Phe Leu Gly Ala Thr Thr Pro Ala Leu Ala<br>        90                            95                          100 | 581 |
| aag ctg cag gtg ccg cgg gag caa ctc tct gaa gtt ctg gag cag att<br>Lys Leu Gln Val Pro Arg Glu Gln Leu Ser Glu Val Leu Glu Gln Ile<br>105                       110                       115                       120 | 629 |
| tgc agt ggt agc tgt ggg ccc atc ttt cga gcc aat atg aac act ggg<br>Cys Ser Gly Ser Cys Gly Pro Ile Phe Arg Ala Asn Met Asn Thr Gly<br>                  125                       130                       135 | 677 |
| gac cct tct aag ccc aag agt gtt att ctc aag gct tta aaa gaa cca<br>Asp Pro Ser Lys Pro Lys Ser Val Ile Leu Lys Ala Leu Lys Glu Pro<br>                     140                       145                       150 | 725 |
| gct ggg ctc cat gag gta caa gat ttc tta ggg cga atc caa ttc cat<br>Ala Gly Leu His Glu Val Gln Asp Phe Leu Gly Arg Ile Gln Phe His<br>                  155                       160                       165 | 773 |
| caa tac ctg ggg aaa cac aaa aac ctg gtg cag ctg gaa ggc tgc tgc<br>Gln Tyr Leu Gly Lys His Lys Asn Leu Val Gln Leu Glu Gly Cys Cys<br>             170                       175                       180 | 821 |
| act gaa aag ctg cca ctc tat atg gtg ttg gag gat gtg gcc cag ggg<br>Thr Glu Lys Leu Pro Leu Tyr Met Val Leu Glu Asp Val Ala Gln Gly<br>185                       190                       195                       200 | 869 |
| gac ctg ctc ggc ttt ctc tgg acc tgt cgg cgg gat gtg atg act atg<br>Asp Leu Leu Gly Phe Leu Trp Thr Cys Arg Arg Asp Val Met Thr Met<br>                  205                       210                       215 | 917 |
| gat ggt ctt ctc tat gat ctc aca gaa aaa caa gta tat cac atc gga<br>Asp Gly Leu Leu Tyr Asp Leu Thr Glu Lys Gln Val Tyr His Ile Gly<br>                     220                       225                       230 | 965 |
| aag cag gtc ctt ttg gcg ctg gaa ttc ctg cag gag aag cat ttg ttc<br>Lys Gln Val Leu Leu Ala Leu Glu Phe Leu Gln Glu Lys His Leu Phe<br>                  235                       240                       245 | 1013 |
| cat ggg gat gtg gca gcc agg aat att ctg atg caa agt gat ctc act<br>His Gly Asp Val Ala Ala Arg Asn Ile Leu Met Gln Ser Asp Leu Thr<br>             250                       255                       260 | 1061 |
| gct aag ctc tgt gga tta ggc ctg gct tat gaa gtt tac acc cga ggg<br>Ala Lys Leu Cys Gly Leu Gly Leu Ala Tyr Glu Val Tyr Thr Arg Gly<br>265                       270                       275                       280 | 1109 |
| gcc atc tcc tct act caa acc ata cct ctc aag tgg ctt gcc cca gaa<br>Ala Ile Ser Ser Thr Gln Thr Ile Pro Leu Lys Trp Leu Ala Pro Glu<br>                  285                       290                       295 | 1157 |
| cgg ctt ctc ctg aga cct gct agc atc aga gca gat gtc tgg tct ttt<br>Arg Leu Leu Leu Arg Pro Ala Ser Ile Arg Ala Asp Val Trp Ser Phe<br>                     300                       305                       310 | 1205 |
| ggg atc ctg ctc tat gag atg gtg act cta gga gca ccg cct tat cct<br>Gly Ile Leu Leu Tyr Glu Met Val Thr Leu Gly Ala Pro Pro Tyr Pro<br>             315                       320                       325 | 1253 |
| gaa gtc cct cct acc agc atc cta gag cat ctc caa aga agg aaa atc<br>Glu Val Pro Pro Thr Ser Ile Leu Glu His Leu Gln Arg Arg Lys Ile<br>             330                       335                       340 | 1301 |
| atg aag aga ccc agt agc tgc aca cat acc atg tac agt atc atg aag<br>Met Lys Arg Pro Ser Ser Cys Thr His Thr Met Tyr Ser Ile Met Lys<br>345                       350                       355                       360 | 1349 |

```
tcc tgc tgg cgc tgg cgt gag gct gac cgc ccc tca cct aga gag ctg    1397
Ser Cys Trp Arg Trp Arg Glu Ala Asp Arg Pro Ser Pro Arg Glu Leu
            365                 370                 375 cgc ttg cgc cta gaa gct gcc att aaa act gca gat gac gag gct gtg    1445
Arg Leu Arg Leu Glu Ala Ala Ile Lys Thr Ala Asp Asp Glu Ala Val
            380                 385                 390 tta caa gta cca gag ttg gtg gta cct gaa ctg tat gca gct gtg gcc    1493
Leu Gln Val Pro Glu Leu Val Val Pro Glu Leu Tyr Ala Ala Val Ala
            395                 400                 405 ggc atc aga gtg gag agc ctc ttc tac aac tat agc atg ctt            1535
Gly Ile Arg Val Glu Ser Leu Phe Tyr Asn Tyr Ser Met Leu
            410                 415                 420 tgaagagtct cgggcaagaa acattcatgc atgagtatat gttcttggaa tcaattcctc  1595
taagaacaga gaatggtctt tcccagggac acaaagggag aaatgggaca tggattcttg  1655
atcttccttt acacatttct cgggaaatct gaaatgatgc tggatgggac tctacacatc  1715
ctgagctaag acatactgtc agtctcactt ctgctgtccc agtcctagaa atcctgggta  1775
gaagtggtgg acctgtgcaa aggaggtttt agaactctgc agtatttgtt ggggcatggc  1835
acaaataagc tcatccctcc cgtccgaggc tagtttcctc tggaaccaca ttttatcta   1895 gatgaaaatt tggaatgaaa tgaaggaata gaaatccaat aaaagagttg aagggaaaga  1955
aaatttaagg ttcttcttgc tcaggattac agatatggac caacacctcc ttcaagaaaa  2015
ggtggtagga cacaaagttc ttcagtcctg agccctacat gtggggttgg aggagaacta  2075
taacggaaaa acctctgagt ttcaccttag gtatagataa agaaagatg gtccccttt    2135 atctgattct gagacaggta aattctgttt gttactacgt ttaattagaa ggtggaggag  2195
tcatttcatg attaagaaca ttcaacatgt attgttcatt aagctagctt cctagttccg  2255
attagactaa ggagactaag cctagagagt caatgttaga acagtgaaaa gaattctgtg  2315
tgtgtgtgtg tgtgtgtgca caataaatag gaaatgtaga aaccaagcaa gaaggcttag  2375
tagctcagtc tttaacaagg gctagaaaag aatgtaatct gatatggaag gatagcagct  2435
tctaattttc aatcatctgt tgatatactg tgaaacttat tttattaaat taatatttat  2495
taaatggaaa tatgcttttc tggtttataa ctactaaaaa tatcataggg aggataaaag  2555
taaataagtg aaagttaatg ccaatagaaa aattcaagag ataatgtaca atgtcagaaa  2615
agggattctt tatgtgtaaa tggggataat acctatttca caaggttgtt ctgaggattg  2675
atacgttttg agtatgtatt tgtacactat ctggcacata tgcgctcaat aaacgtgttt  2735
ctccttttaa aaaaaaaaaa aaaaaaaaaa aaaaaaaaaa aaaaaaaaaa aaaaaaaaaa  2795
aaaaaaaaaa aaaaaaaaaa aaaaaaaaaa aaaaaaaaaa aaaaaaaa              2844

<210> SEQ ID NO 9
<211> LENGTH: 422
<212> TYPE: PRT
<213> ORGANISM: Homo sapiens

<400> SEQUENCE: 9

Met Gly Met Thr Arg Met Leu Leu Glu Cys Ser Leu Ser Asp Lys Leu
1               5                   10                  15

Cys Val Ile Gln Glu Lys Gln Tyr Glu Val Ile Val Pro Thr Leu
            20                  25                  30

Leu Val Thr Ile Phe Leu Ile Leu Leu Gly Val Ile Leu Trp Leu Phe
            35                  40                  45

Ile Arg Glu Gln Arg Thr Gln Gln Gln Arg Ser Gly Pro Gln Gly Ile
        50                  55                  60
```

```
Ala Pro Val Pro Pro Arg Asp Leu Ser Trp Glu Ala Gly His Gly
 65              70                  75                  80

Gly Asn Val Ala Leu Pro Leu Lys Glu Thr Ser Val Glu Asn Phe Leu
                 85                  90                  95

Gly Ala Thr Thr Pro Ala Leu Ala Lys Leu Gln Val Pro Arg Glu Gln
            100                 105                 110

Leu Ser Glu Val Leu Glu Gln Ile Cys Ser Gly Ser Cys Gly Pro Ile
        115                 120                 125

Phe Arg Ala Asn Met Asn Thr Gly Asp Pro Ser Lys Pro Lys Ser Val
    130                 135                 140

Ile Leu Lys Ala Leu Lys Glu Pro Ala Gly Leu His Glu Val Gln Asp
145                 150                 155                 160

Phe Leu Gly Arg Ile Gln Phe His Gln Tyr Leu Gly Lys His Lys Asn
                165                 170                 175

Leu Val Gln Leu Glu Gly Cys Cys Thr Glu Lys Leu Pro Leu Tyr Met
            180                 185                 190

Val Leu Glu Asp Val Ala Gln Gly Asp Leu Leu Gly Phe Leu Trp Thr
        195                 200                 205

Cys Arg Arg Asp Val Met Thr Met Asp Gly Leu Leu Tyr Asp Leu Thr
    210                 215                 220

Glu Lys Gln Val Tyr His Ile Gly Lys Gln Val Leu Ala Leu Glu
225                 230                 235                 240

Phe Leu Gln Glu Lys His Leu Phe His Gly Asp Val Ala Ala Arg Asn
                245                 250                 255

Ile Leu Met Gln Ser Asp Leu Thr Ala Lys Leu Cys Gly Leu Gly Leu
            260                 265                 270

Ala Tyr Glu Val Tyr Thr Arg Gly Ala Ile Ser Ser Thr Gln Thr Ile
        275                 280                 285

Pro Leu Lys Trp Leu Ala Pro Glu Arg Leu Leu Leu Arg Pro Ala Ser
    290                 295                 300

Ile Arg Ala Asp Val Trp Ser Phe Gly Ile Leu Leu Tyr Glu Met Val
305                 310                 315                 320

Thr Leu Gly Ala Pro Pro Tyr Pro Glu Val Pro Pro Thr Ser Ile Leu
                325                 330                 335

Glu His Leu Gln Arg Arg Lys Ile Met Lys Arg Pro Ser Ser Cys Thr
            340                 345                 350

His Thr Met Tyr Ser Ile Met Lys Ser Cys Trp Arg Trp Arg Glu Ala
        355                 360                 365

Asp Arg Pro Ser Pro Arg Glu Leu Arg Leu Arg Leu Glu Ala Ala Ile
    370                 375                 380

Lys Thr Ala Asp Asp Glu Ala Val Leu Gln Val Pro Glu Leu Val Val
385                 390                 395                 400

Pro Glu Leu Tyr Ala Ala Val Ala Gly Ile Arg Val Glu Ser Leu Phe
                405                 410                 415

Tyr Asn Tyr Ser Met Leu
            420

<210> SEQ ID NO 10
<211> LENGTH: 51
<212> TYPE: DNA
<213> ORGANISM: Artificial
<220> FEATURE:
<223> OTHER INFORMATION: An artificially synthesized oligonucleotide for
      siRNA
```

-continued

```
<400> SEQUENCE: 10
caccggtggt acctgaactg tatttcaaga gaatacagtt caggtaccac c         51

<210> SEQ ID NO 11
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 11
aaaaggtggt acctgaactg tattctcttg aaatacagtt caggtaccac c         51

<210> SEQ ID NO 12
<211> LENGTH: 47
<212> TYPE: DNA
<213> ORGANISM: Artificial
<220> FEATURE:
<223> OTHER INFORMATION: siRNA hairpin design

<400> SEQUENCE: 12
ggtggtacct gaactgtatt tcaagagaat acagttcagg taccacc             47

<210> SEQ ID NO 13
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 13
caccggtgga ggagtcattt catttcaaga gaatgaaatg actcctccac c         51

<210> SEQ ID NO 14
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 14
aaaaggtgga ggagtcattt cattctcttg aaatgaaatg actcctccac c         51

<210> SEQ ID NO 15
<211> LENGTH: 47
<212> TYPE: DNA
<213> ORGANISM: Artificial
<220> FEATURE:
<223> OTHER INFORMATION: siRNA hairpin design

<400> SEQUENCE: 15
ggtggaggag tcatttcatt tcaagagaat gaaatgactc ctccacc             47

<210> SEQ ID NO 16
<211> LENGTH: 51
<212> TYPE: DNA
<213> ORGANISM: Artificial
<220> FEATURE:
<223> OTHER INFORMATION: An artificially synthesized oligonucleotide for
      siRNA
```

-continued

```
<400> SEQUENCE: 16
caccgcgcgc tttgtaggat tcgttcaaga gacgaatcct acaaagcgcg c                51

<210> SEQ ID NO 17
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 17
aaaagcgcgc tttgtaggat tcgtctcttg aacgaatcct acaaagcgcg c                51

<210> SEQ ID NO 18
<211> LENGTH: 47
<212> TYPE: DNA
<213> ORGANISM: Artificial
<220> FEATURE:
<223> OTHER INFORMATION: siRNA hairpin design

<400> SEQUENCE: 18
gcgcgctttg taggattcgt tcaagagacg aatcctacaa agcgcgc                     47

<210> SEQ ID NO 19
<211> LENGTH: 22
<212> TYPE: DNA
<213> ORGANISM: Artificial
<220> FEATURE:
<223> OTHER INFORMATION: An artificial synthesized promer seqence for
      making partial length STYK1

<400> SEQUENCE: 19
agagaacaaa gaactcaaca gc                                                22

<210> SEQ ID NO 20
<211> LENGTH: 23
<212> TYPE: DNA
<213> ORGANISM: Artificial
<220> FEATURE:
<223> OTHER INFORMATION: An artificial synthesized primer seqence for
      making partial length STYK1

<400> SEQUENCE: 20
tcataaagcc ttgagaataa cac                                               23
```